United States Patent
Radlein et al.

(10) Patent No.: US 9,896,390 B2
(45) Date of Patent: Feb. 20, 2018

(54) METHODS OF UPGRADING BIOOIL TO TRANSPORTATION GRADE HYDROCARBON FUELS

(71) Applicants: Desmond Radlein, Waterloo (CA); Alain Quignard, Roussillon (FR)

(72) Inventors: Desmond Radlein, Waterloo (CA); Alain Quignard, Roussillon (FR)

(73) Assignees: IFP ENERGIES NOUVELLES, Rueil-Malmaison Cedek (FR); Dynamotive Energy Systems, Vancouver (CA); RADLEIN, DESMOND, Waterloo, Ontario (CA)

( * ) Notice: Subject to any disclaimer, the term of this patent is extended or adjusted under 35 U.S.C. 154(b) by 437 days.

(21) Appl. No.: 14/295,857

(22) Filed: Jun. 4, 2014

(65) Prior Publication Data
US 2014/0288338 A1 Sep. 25, 2014

Related U.S. Application Data

(63) Continuation of application No. 13/822,311, filed as application No. PCT/IB2011/002135 on Sep. 12, 2011, now abandoned.
(Continued)

(51) Int. Cl.
*C07C 1/20* (2006.01)
*C07C 4/02* (2006.01)
(Continued)

(52) U.S. Cl.
CPC .................. *C07C 1/20* (2013.01); *C07C 4/02* (2013.01); *C07C 5/10* (2013.01); *C10G 3/44* (2013.01);
(Continued)

(58) Field of Classification Search
CPC .......... C10G 3/44; C10G 45/04; C10G 47/02; C10G 3/50; C07C 1/20; C07C 4/02; C07C 5/10
See application file for complete search history.

(56) References Cited

U.S. PATENT DOCUMENTS 5,820,640 A * 10/1998 Ikura ...................... C10L 1/328
44/301
2009/0253948 A1 10/2009 McCall et al.
(Continued)

FOREIGN PATENT DOCUMENTS

WO WO-2010 033789 3/2010
WO WO-2010 143980 12/2010

OTHER PUBLICATIONS

International Search Report for PCT/IB2011/002135, Date of the actual completion of the international search: Jun. 28, 2012, dated Jul. 5, 2010.

*Primary Examiner* — Brian McCaig
*Assistant Examiner* — Jason Chong
(74) *Attorney, Agent, or Firm* — Millen, White, Zelano & Branigan, P.C.

(57) ABSTRACT

The present invention relates to the field of biomass derived fuels. It further relates to thermochemical production of liquids (biooils) from biomass. Specifically the present invention relates to methods of upgrading biooil. More specifically it relates to a method for upgrading biooil comprising contacting a dispersed mixture of hydrocarbon liquids, biooil, and partially upgraded biooil, with a transition metal containing catalyst and hydrogen gas at a temperature of around 330° C. and a pressure of about 1700 psi (11.7 MPa) for a period of time sufficient to reduce the oxygen content of the biooil such that it separates on cooling into an aqueous phase and an organic phase, and optionally, to further subject the organic phase to hydrotreating, hydro-
(Continued)

cracking or catalytic cracking to produce a mixture of hydrocarbons boiling in the range of gasoline, diesel and jet fuel.

13 Claims, 11 Drawing Sheets

Related U.S. Application Data

(60) Provisional application No. 61/382,897, filed on Sep. 14, 2010.

(51) Int. Cl.
*C10G 47/02* (2006.01)
*C10G 45/04* (2006.01)
*C10G 3/00* (2006.01)
*C07C 5/10* (2006.01)

(52) U.S. Cl.
CPC ............... *C10G 3/50* (2013.01); *C10G 45/04* (2013.01); *C10G 47/02* (2013.01); *C10G 2300/1014* (2013.01); *C10G 2300/1018* (2013.01); *C10G 2300/1048* (2013.01); *C10G 2300/4081* (2013.01); *C10G 2300/44* (2013.01); *C10G 2400/02* (2013.01); *C10G 2400/04* (2013.01); *C10G 2400/08* (2013.01); *Y02P 30/20* (2015.11)

(56) References Cited

U.S. PATENT DOCUMENTS

| | | |
|---|---|---|
| 2009/0299112 A1 | 12/2009 | Bauer et al. |
| 2010/0314295 A1* | 12/2010 | Sandstede ................ B01J 21/18 208/143 |
| 2011/0054230 A1* | 3/2011 | Cole ........................ C10G 3/45 585/240 |
| 2011/0245554 A1 | 10/2011 | Huber et al. |

* cited by examiner

METHODS OF UPGRADING BIOOIL TO TRANSPORTATION GRADE HYDROCARBON FUELS

FIELD OF THE INVENTION

The present invention relates to the fields of biofuels, biomass liquefaction and biomass pyrolysis, and a method for converting liquefied biomass to liquid hydrocarbon biofuels.

Specifically, it relates to a method for producing motor-grade liquid biofuels from biomass derived liquids by an optional two-stage catalytic process.

BACKGROUND

Biooils are liquid products obtained by thermochemical liquefaction of lignocellulosic biomass materials. Thermochemical methods generally convert biomass into liquid, gaseous and solid products. Among them, so-called fast or flash pyrolysis methods aim to maximize the liquid yield. In fast pyrolysis, biomass, possibly finely divided, is heated rapidly to temperatures above about 400° C. and the liquid products condensed as biooil. Ringer et al. (*Large-Scale Pyrolysis Oil Production: A Technology Assessment and Economic Analysis*, M. Ringer, V. Putsche, and J. Scahill, NREL Technical Report NREL/TP-510-37779, November 2006) have discussed the various technologies that have been deployed for large scale biomass fast pyrolysis. They include bubbling fluidized beds, circulating fluidizing beds, ablative pyrolysis, vacuum pyrolysis, and rotating cone pyrolysis reactors. They point out that so long as the heat transfer requirements are met the chemical nature of the biooil product will be reasonably consistent between pyrolysis processes.

Prima facie, biooils could, in principle, provide low cost renewable liquid fuels; indeed their use as fuel for boilers, as well as for stationary gas turbines and diesels, have all been demonstrated. Furthermore fast pyrolysis has been demonstrated at fairly large scales, of the order of several hundred tons per day. Nevertheless there has not been any significant commercial uptake of this technology.

The reasons relate mostly to the poor physical and chemical properties of biooils in general and fast pyrolysis biooils in particular. For example, some of the undesirable properties of pyrolysis biooils are: (1) corrosivity on account of their high water and acidic contents; (2) a relatively low specific calorific value on account of the high oxygen content, which typically is around 40% by mass; (3) chemical instability on account of the abundance of reactive functional groups like the carbonyl group and phenolic groups that can lead to polymerization on storage and consequent phase separation; (4) a relatively high viscosity and susceptibility to phase separation under high shear conditions, for instance in a nozzle; (5) incompatibility with, on account of insolubility in, conventional hydrocarbon based fuels; (6) adventitious char particles, which will always be present in unfiltered biooil to a greater or lesser degree, can cause blockages in nozzles and pipes. All these aspects combine to render biooil handling, shipping storage and usage difficult and expensive and to make integration into current heat and power producing systems and technologies problematic.

The economic viability of biooil production for energy applications therefore depends on finding appropriate methods to upgrade it to a higher quality liquid fuel at a sufficiently low cost. Indeed, considerable effort has been devoted in recent decades to the search for practical technologies that can overcome some or all of the limitations mentioned.

One suggested approach is to esterify and acetalize biooil with alcohols like ethanol and butanol (e.g. EP0718392 and *Upgrading of Flash Pyrolysis Oil by Reactive Distillation Using a High Boiling Alcohol and Acid Catalysts*, F. H. Mahfud, I. Melián-Cabrera, R. Manurung and H. J. Heeres, Trans. IChemE, Part B, 85 (B5) 466-472, 2007). However the reaction products still have high acidity and significant water content, while the increase in specific heating value is modest. Furthermore the products themselves also tend to be chemically unstable and reactive.

Another approach is to emulsify the biooil in diesel fuels using suitable surfactants (e.g. U.S. Pat. No. 5,820,640 and *Development of emulsions from biomass pyrolysis liquid and diesel and their use in engine—Part 1: emulsion production*, D. Chiaramonti et al, Biomass and Bioenergy 25, 85-99 (2003); *Development of emulsions from biomass pyrolysis liquid and diesel and their use in engines—Part 2: tests in diesel engines*, D. Chiaramonti et al, Biomass and Bioenergy 25, 101-11, (2003)). While this resolves the problem of compatibility with industrial hydrocarbon fuels, it introduces new issues such as emulsion stability while problems related to chemical stability and corrosivity remain.

In yet another approach nascent uncondensed biooil is deoxygenated by conducting it over zeolite catalysts to directly produce low molecular weight aromatics like BTX (benzene, toluene, xylene) from biooil (e.g. U.S. Pat. No. 4,308,411, 1981 and *Green Gasoline by Catalytic Fast Pyrolysis of Solid Biomass Derived Compounds*, T. R. Carlson, T. P. Vispute, and G. W. Huber, ChemSusChem, 1, 397-400 (2008)). However zeolite catalysts are acidic and oxygen is removed largely by dehydration to give water. Consequently, on account of the inherent molar deficiency of hydrogen relative to oxygen and carbon in biooil, yields are relatively low and coke formation is high, adversely affecting the technological difficulty and economic performance.

An indirect approach involves gasification of the biooil (and/or the char co-product) to syngas and subsequent Fischer-Tropsch synthesis of long chain hydrocarbons or olefins from the syngas in a so-called Biomass To Liquids (BTL) process (e.g. the Bioliq process described by Henrich et al. (*Cost estimate for biosynfuel production via biosyncrude gasification*, E. Henrich, N. Dahmen and E. Dinjus, Biofuels, Bioprod. Bioref. 3:28-41 (2009)). However overall yields of hydrocarbons from biomass are rather low and capital costs are high. Furthermore the minimum scales at which BTL processes are predicted to be economic are large relative to the typical local availability of biomass, which necessitates complex logistics for biomass delivery with substantial transportation costs.

Over the last two decades, the approach of direct hydroprocessing of biooil to convert it to stable oxygenates or hydrocarbons has been studied intensively. Elliott has published a comprehensive review of these many historical efforts, including work with model compounds known to be present in biooil (*Historical Developments in Hydroprocessing BioOils*, D. C. Elliott, Energy & Fuels 2007, 21, 1792-1815).

A major obstacle to the catalytic hydroprocessing of biooil has been its propensity to polymerize under heating above about 100° C., leading ultimately to the formation of extraneous solids or coke at temperatures above about 140° C., with consequences like reactor plugging and catalyst deactivation.

Pyrolytic Lignin

These difficulties can be partially circumvented by hydroprocessing only the thermally resistant portion of the biooil. Thus by adding water to biooil it can be separated into an aqueous phase and, usually between 20 and 30% of, a viscous higher density phase, so-called pyrolytic lignin as it is largely derived from the lignin fraction of the biomass pyrolysis feedstock. Since pyrolytic lignin is rich in phenolic material it has much greater thermal stability than the carbohydrate derived portion of the biooil and consequently is easier to catalytically hydroprocess without solids formation. This was the approach taken by Piskorz et al (*Conversion of Lignins to Hydrocarbon Fuels*, J. Piskorz, P. Majerski, D. Radlein, and D. S. Scott, Energy & Fuels, Vol 3, 723-726, 1989) and more recently by Marker and Petri (U.S. Pat. No. 7,578,927, 2009). However in this case one must confront the problem of what to do with the greater, water soluble, portion of the biooil.

Whole Biooil

In order to hydroprocess whole biooil, Elliott et al (U.S. Pat. No. 4,795,841, 1989) proposed to minimize these problems by a two-staged process in the first stage of which the overall thermal stability of the biooil is enhanced by catalytic hydrogenation at a low temperature (~280° C.).

More recent progress in biooil hydroprocessing is illustrated by the work of Heeres et al (*Hydrotreatment of Fast Pyrolysis Oil Using Heterogeneous Noble-Metal Catalysts*, J. Wildschut, F. H. Mahfud, R. H. Venderbosch, and H. J. Heeres, Ind. Eng. Chem. Res., 48 (23), 10324-10334 (2009)), who reported batch experiments in which a comparison was made between mild hydrogenation and deep hydrotreating of biooil over various noble metal as well as conventional Co—Mo and Ni—Mo hydrotreating catalysts. Mild hydrogenation at 250° C. and 100 bar gave single phase liquid products with oxygen contents variously between 18 to 27% and in yields between 21 and 55 mass % (dry basis). However substantial solid by-products (char/coke) were formed while the oxygen content of these oils remained high, between 18 and 27 mass %. On the other hand deep hydrotreatment at 350° C. and 200 bar using gave varying degrees of solid by-products along with one or more oil phases with an average oxygen content of 5 to 11 mass %. They concluded that on the basis of oil yields, deoxygenation levels, and extents of hydrogen consumption, Ru/C seemed to be the most promising catalyst for further testing. Under deep hydrotreatment the hydrogen consumption for this catalyst was estimated to be about 3.6 mass % of the biooil on a dry basis. The lighter of the two products oils had a density of 0.9 g/cm$^3$, water content of 1.5 mass %, oxygen content of 4.8 mass % and a higher heating value of 42.6 MJ/kg.

These results indicate that besides the issues of solids formation and rapid catalyst deactivation, biooil hydroprocessing is also rendered difficult by the formation of multiple oil phases besides the aqueous phase. In addition, the kinetics of hydrogenation are slow, especially at the relatively low temperatures required for thermal stabilization of biooil, and moreover, hydrogen consumption is high.

Baldauf et al. (W. Baldauf, U. Balfanz and M. Rupp, *Upgrading of flash pyrolysis oil and utilization in refineries*, Biomass and Bioenergy, Vol. 7, pp. 237-244, 1994) described the direct hydrodeoxygenation of a flash pyrolysis biooil over commercial CoMo and NiMo catalysts in a packed bed reactor and reported that "the process is restricted by several operational problems such as rapid catalyst deactivation, coking and plugging". Biooil has also been co-processed with a hydrocarbon solvent. Thus, as reported by Elliott (*Historical Developments in Hydroprocessing BioOils*, D. C. Elliott, Energy & Fuels 2007, 21, 1792-1815) Churin et al. (Churin, E.; Grange, P.; Delmon, B. *Quality Improvement of Pyrolysis Oils*; final report on contract no. EN3B-0097-B for the Directorate-General Science, Research and Development, Commission of the European Communities, 1989) co-processed biooil in a 1:1 ratio with the hydrogen donor solvent tetralin. They concluded that this led to a marked improvement in the quality of the product, and the catalysts were less deactivated by coke deposition, which was attributed to the hydrogen donor properties of the solvent.

US2009/0253948 discloses a process for the conversion of biomass derived pyrolysis oil to liquid fuel by two-stage deoxygenation of the pyrolysis oil and separation of the products and in which the final hydrocarbon product may be recycled. However it does not teach the high dispersal or solubilization of pyrolysis oil in a hydrocarbon medium with the consequent benefits of a large increase in reaction rates and catalyst lifetime."

Nevertheless an efficient hydrotreating process has yet to emerge. The difficulties that have been encountered have their root in the rapid thermal polymerization of biooil that leads to fast catalyst deactivation. In other words, at the temperatures typically required for hydroprocessing of biooil, polymerization reactions are substantially faster than the competing hydroprocessing reactions, ultimately leading to coke formation.

Indeed, in a recent study of biooil stabilization by hydrogenation, Venderbosch et al (*Stabilization of biomass-derived pyrolysis oils*, R. H. Venderbosch, A. R. Ardiyanti, J. Wildschut, A. Oasmaa and H. J. Heeres, J. Chem. Technol. Biotechnol. 2010, 85: 674-686) 2010) came to similar conclusions, stating that: "In hydroprocessing of biooils, a pathway is followed by which pyrolysis oils are further polymerized if H2 and/or catalyst is absent, eventually to char components, or, with H2/catalyst, to stabilized components that can be further upgraded."

Therefore, what is required is an improved process for biooil hydroprocessing that minimizes the formation of solids and catalyst deactivation, minimizes hydrogen consumption and maximizes space-time yield of deoxygenated oil product. It is also desirable to maximize the fraction of hydrocarbon product that boils in the range of useful fuels like gasoline or diesel. A preferred process would have the further following desirable characteristics:

1) Convert biooil to high value hydrocarbon products, especially motor fuels.
2) Minimize hydrogen consumption.
3) Operate at conditions that minimize the coke formation that leads to catalyst deactivation and/or reactor plugging.
4) Maximize reaction kinetics to reduce required reactor volumes and associated capital and operating costs and maximize throughput/productivity.
5) Make operating conditions as mild as possible to further reduce capital and operating costs.
6) The process should accommodate a wide range of biomass-derived liquids, and biomass pyrolysis liquids in particular, that may have wide ranges of viscosity, water content and degree of polymerization depending on the feedstock and pyrolysis process.
7) Any catalyst employed should be low-cost and long-lived.
8) Preferably it should be possible to implement the process with existing reactor technologies.

9) Preferably the method should accommodate co-processing with petroleum derived hydrocarbon feedstocks for compatibility with oil refineries.

The inventive process disclosed herein meets all these criteria.

SUMMARY OF THE INVENTION

The invention relates to a process for producing transportation liquid biofuels and/or chemicals from biomass derived liquids. More specifically, the invention relates to a process for upgrading biooils into motor-grade liquid biofuels for air, marine or ground transportation applications, by a hydroreforming step, optionally followed by a hydrotreatment and/or hydrocracking/hydroconversion step.

In its broadest aspect, the invention relates to a method for converting a feed containing biooil comprising dispersing the feed in a hydrocarbon liquid with the aid of a dispersing agent and subjecting the dispersion to a hydroreforming step with hydrogen under pressure in the presence of a catalyst in order to obtain an aqueous phase and at least one organic phase containing partially upgraded biooil and hydrocarbon liquid.

We have now surprisingly discovered that dispersion of biooil in a hydrocarbon rich medium with the aid of a dispersing agent facilitates its conversion into hydrocarbons and stable oxygenated hydrocarbons without significant formation of coke or biooilpolymers, with low rates of catalyst deactivation and significantly enhanced conversion rates. The reaction is here designated as "hydroreforming" since it results in a distinctive change in the molecular weight distribution of the biooil. The product of hydroreforming is a hydrocarbon rich mixture consisting of partially upgraded biooil (PUB) together with hydrocarbons. It is designated herein as UBA. Fresh UBA is a transparent light amber coloured liquid that darkens on exposure to air, nevertheless without any noticeable change in other physico-chemical properties.

Furthermore, we have also discovered that the partially upgraded biooil product of hydroreforming is readily converted to essentially fully deoxygenated, motor fuel grade hydrocarbons using conventional refinery processes including hydrotreating, hydrocracking. The hydrocarbon product of this second step will be designated herein as UBB.

In the hydroreforming step some internal reforming of biooil to hydrogen and carbon oxides does take place with a relatively high yield of hydrocarbons and a relatively low consumption of hydrogen. Therefore, hydrogen consumption is moderate in the hydroreforming step and the internal hydrogen production via hydroreforming allows the process to be run with very limited hydrogen consumption.

During the hydroreforming step, the biooil is hydrotreated to stabilize the product, render it miscible with hydrocarbons, cause phase separation of water in the biooil, lower its viscosity, lower its corrosivity and lower its oxygen content from about 50 mass % to less than 15 mass %.

The hydroreforming step presents the following advantages:

The biooil is stabilized so it can be hydrotreated in a refinery without the risk of coke formation.

It is deoxygenated to a sufficient degree to render it miscible with typical refinery hydrotreater feeds.

The oxygen content is substantially reduced so that any further hydrogen requirements during hydrotreatment at a refinery are strongly decreased to a level suitable with conventional petroleum product hydrotreatment/hydrocracking processes.

Hydrogen is internally generated from the water present by hydroreforming a portion of the biooil so that most of the oxygen is released as carbon dioxide and the net hydrogen requirement is very small.

The product is essentially water free as the residual water forms a separate phase.

The corrosiveness of the product is strongly decreased since most of the organic acids remain in the water phase.

Light carboxylic acids like acetic acid present in the raw biooil can be recovered as valuable by-products.

Only a small amount of gaseous hydrocarbons like methane (that represent a waste of both carbon and hydrogen) are formed.

If needed this methane fraction can be reformatted by the so called Steam Methane Reforming process (SMR), to produce bio-hydrogen for either the hydroreforming or hydrotreatment/hydrocracking processes.

There is also a possibility to use the biochar proceeding from the pyrolysis step as a gasifier feedstock to produce synthetic gas ($CO+H_2$). This synthetic gas can also be used to produce bio-hydrogen for either the hydroreforming or hydrotreatment/hydrocracking processes.

In this way, using SMR and/or biochar gasification, the upgrading process can be hydrogen self sufficient without any need of hydrogen from fossil origin.

The yield towards hydrocarbon is higher than by the direct hydrodeoxygenation route.

Process conditions are relatively mild and the hourly space velocity is high (shorter residence time than in conventional hydrodeoxygenation processes) in continuous mode. Together with the higher hydrocarbon yield and the reduced requirements for hydrogen it is expected to decrease both the capital and the operating costs to upgrade the biooils to produce renewable source of transportation fuels and chemicals from whole ligno-cellulosic biomass.

UBA can either be directly utilized in blends with hydrocarbon fuels for industrial stationary power and heating applications or be further upgraded to transportation grade liquid hydrocarbon fuels (gasoline/jet fuel/diesel/marine distillate fuel) in a further hydrotreating or hydrocracking/hydroconversion process. It can also be used as a primary source for chemicals.

Specifically, the present invention relates to a method for treating a feed containing biooil comprising:

dispersing the feed containing biooil in a hydrocarbon type liquid with the aid of a dispersing agent, subjecting the dispersion so obtained to a hydroreforming step with hydrogen under pressure in the presence of at least one transition metal catalyst, separating the effluent from the hydroreforming step in an aqueous phase and at least one organic phase containing partially upgraded biooil and hydrocarbon type liquid.

Preferably, the hydroreforming step is carried out at a temperature from about 250° C. to about 450° C. and at an absolute pressure between about 3.4-27.6 MPa (500 and 4000 psi), preferably between about 3.4-20.7 MPa (500 and 3000 psi), and even more preferably between about 6.9-13.8 MPa (1000 to 2000 psi).

Preferably, the dispersing agent is a surfactant, preferably a non ionic surfactant, or an oxygen-containing solvent, pure or blended, or any hydrocarbon type liquid product containing oxygen (such as tar oil from coal gasification or from coal pyrolysis or from coal direct liquefaction process), or recycled partially upgraded biooil phase with or without the hydrocarbon liquid in the organic phase from the hydroreforming step.

Preferably, the hydrocarbon liquid is selected from an aromatic hydrocarbon solvent, a naphthenic hydrocarbon solvent, a naphtheno-aromatic hydrocarbon solvent, a fossil or biomass fuel derived hydrocarbon liquid and/or recycled hydrocarbon liquid obtained from further hydrotreatment and/or hydrocracking and/or mild hydrocracking step(s) of the upgraded biooil.

Most preferably, the dispersing agent is recycled partially upgraded biooil phase with or without the hydrocarbon liquid contained in the organic phase and the hydrocarbon liquid is recycled hydrocarbon liquid UBB obtained from the further hydrotreatment and/or hydrocracking and/or mild hydrocracking step(s).

Preferably, the catalyst used in the hydroreforming step comprises at least one transition metal from group 3 to group 12. The metal comprises preferably a group 10 metal, singly or in combination with at least one metal selected from group 3 to group 12 of the periodic table, more preferably Ni, singly or in combination with at least one metal selected from Ce, Zr, Cr, Mo, W, Mn, Re, Fe, Ru and Cu, even more preferably Ni, NiCr or NiMn. The catalyst is preferably supported on a support, preferably the support is porous carbon. Most preferably, the catalyst is Ni, NiCr or NiMn on porous carbon.

Preferably, the organic phase contains less than about 15 mass % oxygen and less than about 2 mass % water. Preferably, the hydrogen consumption in the hydroreforming step is less than about 2% of the mass of the biooil.

Preferably, the biooil is produced by fast or flash pyrolysis from biomass feedstock.

Optionally, the partially upgraded biooil phase with or without the hydrocarbon type liquid contained in the organic phase is further subjected to a hydrotreatment step in the presence of hydrogen and a hydrotreating catalyst at a temperature between 250° C. and 450° C., at a pressure between 2 MPa and 25 MPa (290-3625 psi) and at an hourly space velocity between 0.1 h-1 and 20 h-1 and/or to a hydrocracking step in the presence of hydrogen and a hydrocracking catalyst at a temperature over 200° C., preferably between 250° C. and 480° C., at a pressure between 2 MPa and 25 MPa (290-3625 psi) and at an hourly space velocity between 0.1 h-1 and 20 h-1 and/or to a mild hydrocracking step in the presence of hydrogen and a hydrocracking catalyst at a temperature between 250° C. and 480° C., at a pressure between 2 MPa and 12 MPa and an hourly space velocity between 0.1 h-1 and 20 h-1 to produce a mixture of hydrocarbons boiling in the range of gasoline, jet fuel and diesel.

Optionally, the partially upgraded biooil phase with or without the hydrocarbon type liquid contained in the organic phase is co-processed with fossil derived feedstock.

Optionally, the effluent obtained from the further hydrotreatment and/or hydrocracking and/or mild hydrocracking step(s) is further subjected to a high pressure hydrocracking step in the presence of hydrogen and a hydrocracking catalyst at a temperature between 250° C. and 480° C., at a pressure between 2 MPa and 25 MPa (290-3625 psi) and an hourly space velocity between 0.1 h-1 and 20 h-1.

DETAILED DESCRIPTION

Hydroreforming

Feed

Figure 1:
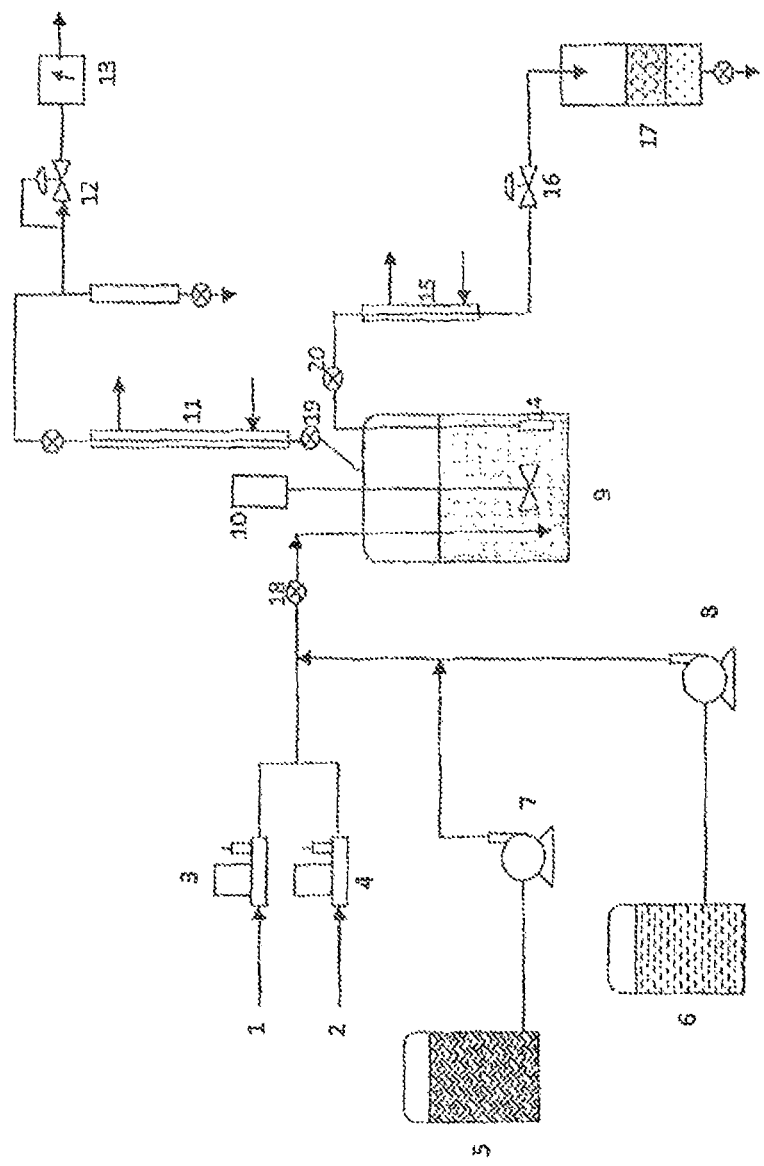
FIG. 1 illustrates the experimental arrangement for the tests described herein for Step 1. It may be operated in either batch or semi-continuous mode.

The feed contains biooil. Biooil is a complex mixture of compounds, including oxygenates, that are obtained from the breakdown of biopolymers in biomass. In the case of lignocellulosic biomass, the structures of the three major components, cellulose, hemicellulose and lignin, are well represented by the biooil components.

Biooils can be derived from plants such as grasses and trees, wood chops, chaff, grains, grasses, corn, corn husks, weeds, aquatic plants, hay and other sources of lignocellulosic material, such as derived from municipal waste, food processing wastes, forestry wastes and cuttings, energy corps, or agricultural and industrial wastes (such as sugar cane bagasse, oil palm wastes, sawdust or straws). Biooils can also be derived from pulp and paper by products (recycled or not).

Biooil is a highly oxygenated, polar hydrocarbon product that typically contains at least about 10 mass % oxygen, typically about 10 to 60 mass %, more typically about 40 to 50 mass % oxygen. In general, the oxygenates will be alcohols, aldehydes, actetates, ethers, organic acids and aromatic oxygenates. Some of the oxygen is present as free water which constitutes at least about 10 mass %, typically about 25 mass % of the biooil. These properties render biooil totally immiscible with fuel grade hydrocarbons, even with aromatic hydrocarbons, which typically contain little or no oxygen.

Biooils are obtained by thermochemical liquefaction, notably pyrolysis, such as flash, fast, slow or catalytic pyrolysis. Pyrolysis is a thermal decomposition in the absence of oxygen with a thermal cracking of the feedstocks towards gas, liquid and solid product. A catalyst can be added to enhance the conversion in the so called catalytic pyrolysis. Catalytic pyrolysis generally leads to biooil having a lower oxygen content than biooil obtained by thermal decomposition. The selectivity between gas, liquid and solid is well related to the reaction temperature and vapor residence time. Biomass pyrolysis processes, especially fast or flash pyrolysis, are well described in the literature (A. V. Bridgewater, H. Hofbauer and S. van Loo, *Thermal Biomass*

*Conversion*, CPL Press, 2009, 37-78). Lower temperature (around 400° C.) and longer residence time (a few minutes to a few hours), obtained by slow pyrolysis, favor the production of solid product, also called char or char coal, with typically 35 wt % gas, 30 wt % liquid, 35 wt % char. Very high temperature above 800° C. used in the gasification processes favour gas production (typically more than 85 wt %). Intermediate reaction temperature (typically 450° C.-550° C.) and short vapor residence time (typically 10-20 s), for the intermediate pyrolysis, favor the liquid yield: typically 30 wt % gas, 50 wt % liquid, 20 wt % char. Intermediate reaction temperature (typically 450° C.-550° C.) and very short vapor residence time (typically 1-2 s) for the so called flash pyrolysis or fast pyrolysis, favor even more the liquid yield: typically 10-20 wt gas, 60-75 wt % liquid, 10-20 wt % char. The highest liquid yields are obtained by the flash pyrolysis processes, with up to 75 wt %.

This is the reason why, preferably, biooils used in the present invention are obtained by fast or flash pyrolysis from a biomass feedstock.

The feed in the present process can further contain other oxygenates derived from biomass such as vegetable oils or animal fat derived oils. Vegetable oil or animal fat derived oil comprises fatty matter and therefore correspond to a natural or elaborate substance of animal or vegetable origin, mainly containing triglycerides. This essentially involves oils from renewable resources such as fats and oils from vegetable and animal resources (such as lard, tallow, fowl fat, bone fat, fish oil and fat of dairy origin), as well as the compounds and the mixtures derived therefrom, such as fatty acids or fatty acid alkyl esters. The products resulting from recycling of animal fat and of vegetable oils from the food processing industry can also be used, pure or in admixture with other constituent classes described above. The preferred feeds are vegetable oils from oilseed such as rape, erucic rape, soybean, jatropha, sunflower, palm, copra, palm-nut, arachidic, olive, corn, cocoa butter, nut, linseed oil or oil from any other vegetable. These vegetable oils very predominantly consist of fatty acids in form of triglycerides (generally above 97% by mass) having long alkyl chains ranging from 8 to 24 carbon atoms, such as butyric fatty acid, caproic, caprylic, capric, lauric, myristic, palmitic, palmitoleic, stearic, oleic, linoleic, linolenic, arachidic, gadoleic, eicosapentaenoic (EPA), behenic, erucic, docosahexaeoic (DHA) and lignoceric acids. The fatty acid salt, fatty acid alkyl ester and free fatty acid derivatives such as fatty alcohols that can be produced by hydrolysis, by fractionation or by transesterification for example of triglycerides or of mixtures of these oils and of their derivatives also come into the definition of the "oil of vegetable or animal origin" feed in the sense of the present invention. All products or mixtures of products resulting from the thermochemical conversion of algae or products from the hydrothermal conversion of lignocellulosic biomass or algae (in the presence of a catalyst or not) or pyrolytic lignin are also feeds that can be used.

Moreover, the feed containing biooil can be coprocessed with petroleum and/or coal derived hydrocarbon feedstocks. Since hydrogen is internally produced in the hydroreforming step of biooil, the hydrogen consumption for coprocessing with petroleum and/or coal derived hydrocarbon feedstocks is thus reduced. The petroleum derived hydrocarbon feed stock can be straight run vacuum distillates, vacuum distillates from a conversion process such as those from coking, from fixed bed hydroconversion or from ebullating bed heavy fraction hydrotreatment processes, or from solvent deasphalted oils. The feeds can also be formed by mixing those various fractions in any proportions in particular deasphalted oil and vacuum distillate. They can also contain products from the fluid catalytic cracking units, such as Light Cycle Oil (LCO) of various origins, Heavy Cycle Oil (HCO) of various origins and any distillate fraction from fluid catalytic cracking generally having a distillation range of about 150° C. to about 370° C. They can also contain aromatic extracts and paraffins obtained from the manufacture of lubricating oils. The coal derived hydrocarbon feedstock can be products from the liquefaction of coal. Aromatics fractions from coal pyrolysis or coal gasification can also be used.

The feed containing biooil can contain any mixture of the other feedstocks previously cited.

Dispersion

In the hydroreforming step, a dispersed mixture comprising the feed containing biooil and a hydrocarbon liquid is formed with the help of a dispersing agent.

The hydrocarbon liquid can be selected from an aromatic hydrocarbon solvent, a naphtenic hydrocarbon solvent, a naphtheno-aromatic hydrocarbon solvent, a fossil or biomass fuel derived hydrocarbon liquid and/or recycled UBB, either singly or in mixtures. Preferably the hydrocarbon liquid is present in a concentration of from 20% to 70% by mass, preferably from 20% to 50% by mass, based on the total mass of all components in the composition and wherein the total sum of feed, hydrocarbon liquid and dispersing agent is 100% by mass.

Whereas not limitative, the hydrocarbon solvent can be selected from aromatic hydrocarbon compounds or blends of aromatic solvents (toluene, xylenes, naphthalene and alkyl naphthalenes, fossil aromatic cuts such as aromatic extracts from the lube manufacturing, catalytic cracking gasoils, also know as Light Cycle Oil LCO or Heavy Cycle Oil HCO, aromatic distillates from coal liquefaction, coal pyrolysis or coal gasification, . . . ) or naphtheno-aromatic hydrocarbon compounds (tetralin, partially hydrogenated polyaromatics, partially hydrotreated LCO or HCO, partially hydrotreated distillates from direct coal liquefaction, coal pyrolysis or coal gasification, . . . ) . . . ) or naphthenic hydrocarbon compounds (decalin, fully hydrogenated alkyl naphthalenes, fully hydrotreated LCO or HCO, fully hydrotreated distillates from direct coal liquefaction, coal pyrolysis or coal gasification, . . . ) or a middle distillate from coal direct liquefaction, or any liquid distillate with at least 10% aromatics, preferably at least 25% aromatics.

The fossil or biomass fuel derived hydrocarbon liquid of the process according to the invention is preferably a middle distillate feed. In the sense of the present invention, the term middle distillate designates hydrocarbon fractions whose boiling point temperature ranges between about 130° C. and about 410° C., generally between about 140° C. and about 375° C., for example, between about 150° C. and about 370° C. A middle distillate feed can also comprise a gas oil or diesel cut, or it can be referred to by one of these designations. Although not constituting an exhaustive list, petroleum straight run gas oils or preferably more aromatic gas oils such as those obtained from catalytic cracking (LCO) or from any other residue conversion process (coking, visbreaking, residue hydroconversion, . . . ) or aromatic extract from lube oil manufacturing or liquid distillates proceeding from coal conversion constitute a part of the typical hydrocarbon liquid of the method according to the invention.

Preferably, the hydrocarbon liquid is recycled UBB. This allows to provide a final hydrotreated product (UBB) made up entirely of renewable carbon (i.e. derived from biomass).

The dispersing agent used to form the dispersion can be an oxygen-containing solvent, pure or blended, or a surfactant, or recycled organic phase (UBA) produced by the hydroreforming step as described hereafter, or any hydrocarbon type liquid product containing oxygen, such as tar oil from coal gasification or from coal pyrolysis or from coal direct liquefaction process conducted under high hydrogen pressure and with an hydroconversion catalyst. Its role is to facilitate dispersion of the biooil in the hydrocarbon liquid.

Optionally, the dispersion is facilitated by mechanical means such as a stirrer or a pump.

The dispersing agent can be selected from an oxygen-containing solvent such as alkanol (alcohol such as isopropanol, n-butanol . . . ) or other solvents containing oxygen (such as ketones, esters, phenolic compounds . . . )

The surfactant can be a nonionic polymeric surfactant, preferably one or more surfactants selected from the group consisting of an alkyd polyethylene glycol, for example, Atlox™ 4914 (available from CRODA) and a polyalkylene glycol ether, for example, Atlas™ G-5000. Preferably the nonionic polymeric surfactant is present in a concentration of from 1% to 10% by mass diluted in a petroleum type distillate, preferably with a significant aromatic content such as a n° 2 Diesel fraction or domestic heating oil or any hydrocarbon type liquid distillate from petroleum or coal conversion. This diluent is usually present in concentration from 10% to 300% by mass with respect to biooil, preferably from 25% to 200% by mass, with respect to the biooil.

Preferably, the solvent is recycled organic phase (UBA) produced by the hydroreforming step and containing partially upgraded biooil and the hydrocarbon liquid fraction or recycled partially upgraded biooil without the hydrocarbon liquid fraction from the organic phase (after having been distilled off). Preferably, the solvent is present in a concentration of from 10% to 300% by mass with respect to biooil, preferably from 25% to 100% by mass, with respect to the biooil.

The weight ratio of biooil/dispersing agent/hydrocarbon liquid is preferably from about 2/4/2 to 2/1/0.5.

The presence of the hydrocarbon liquid and the dispersing agent are important features of the invention. Good dispersion of two immiscible phases is enhanced if the interfacial tension between them is low. The lower the interfacial tension between two immiscible phases, the lower the work required to generate new interfacial surface so the finer the drops (higher degree of dispersal) that would form. Biooil is only very poorly soluble in pure hydrocarbons so it is somewhat surprising that in fact the interfacial tension between biooil and hydrocarbons, especially aromatic hydrocarbons, is surprisingly low. Furthermore, surface tension usually decreases linearly with temperature. Both these factors serve to enhance the dispersibility of biooil in hydrocarbon rich media at the typical reaction temperatures during hydroreforming. We note that the pressure dependence of the solubility of hydrogen in a given solvent usually follows Henry's Law. Furthermore, Henry's Law constant varies only weakly with temperature (E. Brunner, *Solubility of Hydrogen in 10 Organic Solvents at 298.15, 323.15, and 373.15 K*, J. Chem. Eng. Date 1985, 30, 269-273) but depends much more strongly on the polarity of the solvent so that the solubility of hydrogen is generally significantly higher in non-polar media like hydrocarbons than in polar solvents. For example, at a specified pressure and at room temperature, hydrogen is about 14 times more soluble, in mole fraction units, in ethanol than in water and about 44 times more soluble in 1-octene than in water (Purwanto, R. M. Deshpande, R. V. Chaudhari, and H. Delmas, *Solubility of Hydrogen, Carbon Monoxide, and 1-Octene in Various Solvents and Solvent Mixtures*, J. Chem. Eng. Data 1996, 41, 1414-1417). Biooil is highly polar since it incorporates a large fraction (40-50 mass %) of oxygen, much of which is present as water. Consequently the solubility of hydrogen in biooil may be expected to be relatively low.

Without wishing to be bound by theory, we conjecture that dispersion of biooil in a hydrocarbon rich medium enhances the availability of hydrogen at catalytic sites where hydrogen transfer to biooil occurs and in this way facilitates its rapid hydroconversion and, consequently, relative suppression of the competing rapid thermally induced reactions that lead to cross-linking and polymerization, to which biooil is prone. This effect is further enhanced, the higher the solubility and consequently the higher the availability of hydrogen in the hydrocarbon rich medium.

Figure 3A:
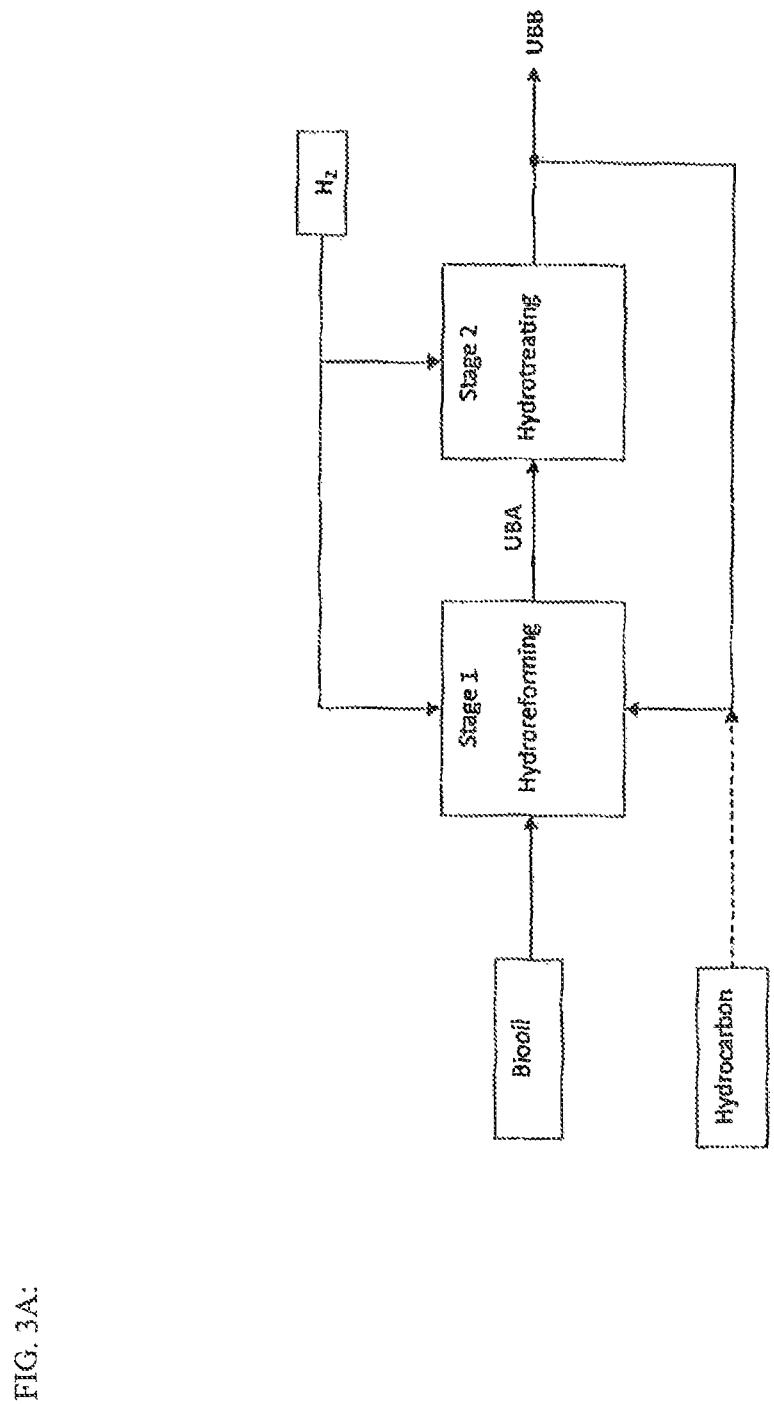
FIG. 3A illustrates a possible scheme for carrying out the process of this invention, in which a part of the product of the second hydrotreating stage is recycled to provide the hydrocarbon required for the first stage.
Figure 3B:
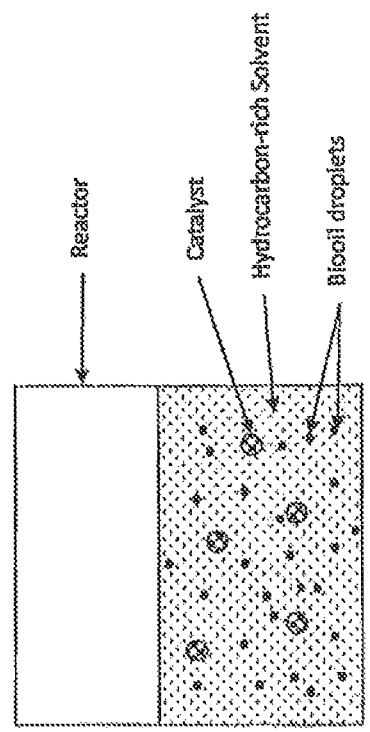
FIG. 3B illustrates the relative disposition of dispersed biooil, catalyst and solvent in a mixed reactor implementation of Stage 1 hydroreforming.

FIG. 3B illustrates the dispositions of the catalyst, biooil dispersion and solvent in a stirred reactor implementation.

Furthermore, since polymerization reactions are necessarily at least bimolecular, another contributing factor may be the reduction in rate of cross-linking reactions caused by a lower effective biooil concentration in the reaction mixture.

A further benefit to the presence of hydrocarbons in the reaction mixture is that they also serve to lower the density of the partially upgraded biooil product of the first stage which facilitates phase disengagement of the partially upgraded biooil from the aqueous phase which separates easily on cooling the reaction mixture.

A still further benefit is that the presence of hydrocarbons in the reaction mixture tends to expel water from the partially upgraded biooil phase so that its water content is as lowered as much as possible, which is conducive to use of the partially upgraded biooil either as an industrial fuel or as a feedstock for further hydrotreating/hydrocracking. Thus, the partially upgraded biooil phase UBA contains less than about 2 mass % of water, preferably less than 1%, more preferably less than 0.5%.

Operating Conditions

The dispersed mixture of the hydrocarbon liquid, the feed containing biooil and the dispersing agent is treated with hydrogen in the presence of a catalyst. The conditions of the hydroreforming are an absolute pressure between about 3.4-27.6 MPa (500 and 4000 psi), preferably between about 3.4-20.7 MPa (500 and 3000 psi), more preferably between about 6.9-13.8 MPa (1000 to 2000 psi) with a temperature from about 250° C. to about 450° C., preferably from about 300° C. to about 400° C., more preferably from about 300° C. to 360° C. and typically about 330° C.

Preferably, the feed containing biooil is not preheated or only preheated to a low level (i.e. <60/80° C.) prior to the hydroreforming step, since prolonged heating or storage at elevated temperatures can cause degradation.

For continuous processing, the process desirably has a relatively high hourly space velocity (HSV) related to the biooil, usually greater than about 0.2 $h^{-1}$, preferably from about 0.5 $h^{-1}$ to about 5 $h^{-1}$, most preferably from about 1 $h^{-1}$ to about 5 $h^{-1}$. In a preferred embodiment, the weight hourly space velocity is greater than about 1 kg of biooil per kg of catalyst per hour.

Reactor Configurations

Apparatus for conducting the process is not limited. The process can be conducted batchwise or continuously. Nevertheless for a large scale industrial application, the continuous operation is preferred.

The hydroreforming reaction may be carried out in any reactor that facilitates efficient dispersion of the biooil feed in the reaction mixture. A simple Continuous Stirred Tank Reactor (CSTR) is suitable in the batchwise mode. For continuous applications, trickle bed, moving bed, ebullated bed or slurry reactors are suitable. The moving bed and ebullated bed reactors have the advantage of allowing easy catalyst replacement in a continuous operation, making more flexible the operability of the unit, increasing the stream factor and keeping an almost constant activity versus time on life. Other effective reactors which embody the principles outlined herein will be envisaged by persons skilled in the art of chemical reactor technology and are within the scope of this invention.

Hydrogen Consumption

The hydrogen consumption of the first stage is moderate. To put this in context, a typical elemental composition of a biooil containing about 25 mass % $H_2O$ may be $CH_{1.87}O_{0.75}$, corresponding to an oxygen content of about 46 mass %. For this case, the following two hypothetical limiting cases can be considered:

1. Complete hydrogenation with externally supplied hydrogen to give a diesel like hydrocarbon product:

1 kg biooil ($CH_{1.87}O_{0.75}$)+0.064 kg $H_2$→0.54 kg "Diesel" (—$CH_2$—)$_x$+0.52 kg $H_2O$
   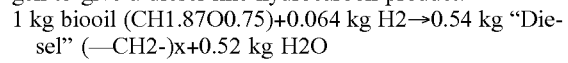
   Yields: 54% Diesel+0% $CO_2$ based on BioOil; 0.06 kg $H_2$ consumed per kg Biooil;

2. All required hydrogen is supplied internally by internal reforming of the biooil with oxygen removed as carbon oxides:

1 kg ($CH_{1.87}O_{0.75}$)→0.35 kg Diesel (—$CH_2$—)$_x$+0.44 kg $CO_2$+0.11 kg CO+0.10 kg $H_2O$
   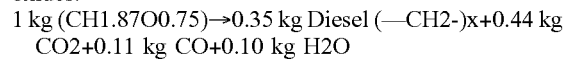
   Yields: 35% Diesel+44% $CO_2$ based on BioOil; 0 kg $H_2$ consumed per kg biooil;

In the first case carbon in biooil is maximally converted to hydrocarbons while in the second case there is no net consumption of hydrogen but at the cost of loss of some carbon as carbon oxides lowering the ultimate yield of hydrocarbons. Since hydrogen gas is relatively expensive and the objective is to minimize the production of water with no economic value and with a significant operating cost for its treatment, an optimal process must balance these two factors. In the inventive process described herein, biooil is transformed to hydrocarbons in the sequence Biooil→UBA→UBB. The overall yield and hydrogen consumption for this sequence are:

Yields (based on biooil): ~25% UBB+~8.4% $CO_2$; ~2.4% $H_2$ consumed per kg Biooil Evidently the inventive process falls within the two limiting cases mentioned above, which indicates that some internal reforming of biooil to hydrogen and carbon oxides does take place, but with a relatively high yield of hydrocarbons and a relatively low consumption of hydrogen. Some of the hydrogen necessary for the reaction is internally generated from the water present in the biooil by hydroreforming a portion of the biooil so that a significant part of the oxygen is released as carbon dioxide and the net hydrogen requirement is much smaller than by direct hydrodeoxydation process. The other part of the hydrogen necessary for the reaction is supplied externally. Typically, the hydrogen consumption in the hydroreforming step is less than about 2 wt % of the mass of the biooil fed into the reactor and the corresponding $CO_2$ emission to produce it is much lower than in hydrodeoxygenation (HDO) type processes with at least 4 or 5 wt % external hydrogen consumption Since the cost of hydrogen is not presently insignificant it is also advantageous to minimize hydrogen usage. Hydrogen can be supplied from fossil resources, i.e. by gasification/partial oxidation or by steam reforming. Furthermore, if the hydrogen requirements, as well as any required process energies, are both ultimately derived from biomass (by steam reforming of the produced methane and light gas and/or light oxygenates fractions from hydroreforming and/or hydrotreatment/hydrocracking steps and/or by gasification/partial oxidation of the pyrolysis char from the flash pyrolysis step), then the inventive process would represent a totally sustainable source of motor fuel and the corresponding $CO_2$ emission is only, or mainly, from biomass origin. Of course hydrogen usage will become a less significant issue if there is a substantial shift to a hydrogen economy since that implies a lower cost of hydrogen.

If the biooil is produced by fast pyrolysis there is a possibility to produce the hydrogen required for upgrading by gasification of the char co-product of pyrolysis. Since typical char yields are around 20 mass % of the biomass fed, and the carbon content of the char is typically greater than 60 mass %, no more than about a third to a half of the co-produced char is theoretically sufficient to produce the required hydrogen. Another option for hydrogen production is steam reforming of the biooil itself, although that implies some loss of carbon efficiency. A better option is steam reforming of the produced methane and light gas and/or light oxygenates fractions from the hydroreforming step or the further hydro-treatment/hydrocracking step. The recovered CO can also be reacted with the produced water to make hydrogen by the well known Water Gas Shift reaction or WGS. In this way the overall process from biomass to UBB could be made self-sufficient in hydrogen.

In some of the cited studies the catalytic stabilization of biooil in preparation for hydrotreating is carried out at relatively low temperatures (<300° C.), e.g. 250° C. for Heeres et al (*Hydrotreatment of Fast Pyrolysis Oil Using Heterogeneous Noble-Metal Catalysts*, J. Wildschut, F. H. Mahfud, R. H. Venderbosch, and H. J. Heeres, Ind. Eng. Chem. Res., 48 (23), 10324-10334 (2009) and ~280° C. in U.S. Pat. No. 4,795,841. One consequence of operation at higher temperatures of the order of 330° C. as contemplated in the present invention, is that reaction kinetics become faster so the space velocity increases, which improves the economics in so far as it leads to shorter reaction times and smaller equipment size.

Energy Balance

Since the HHV (higher heating value) of biooil, UBA and hydrogen are approximately 16 MJ/kg, 30 MJ/kg and 121 MJ/kg respectively, then based on the yields of UBA it was verified that the first stage hydroreforming reaction is approximately thermoneutral. This simplifies reactor engineering considerations and is conducive to improved thermal efficiency for the process.

Catalysts

It is a further advantage of this invention that non-noble metal catalysts have been found to give satisfactory performance for the hydroreforming stage. The catalyst is preferably supported.

Non-limiting examples of particularly suitable catalyst material include one or more transition metals from group 3 to group 12, more specifically metals comprising group 10 metals, for example nickel, singly or in combination with at least one metal selected from group 3 to group 12, preferably group 3, 4, 6, 7, 8, 10, 11, 12 such as Ni, Ni—Zr, Ni—Ce, Ni—Ce—Zr, Ni—Cr, Ni—Mo, Ni—W, Ni—Mn, Ni—Re, Ni—Fe, Ni—Ru, Ni—Cu. A catalyst shall be used which comprises, for example, 1% to 20% by mass of nickel (expressed as nickel oxide NiO), preferably 5% to 15% by mass of nickel singly, or in combination with 0% to 10% by mass of at least a metal selected from group 3 to group 12 including lanthanides. The foregoing catalysts are preferably employed in their reduced form.

Support materials are chosen to bring the active (metal) phase of the catalyst into contact with reactants. Preferably, the support material is porous carbon (such as activated carbon). This support shows no tendency to hydrolyse and deteriorate in water and acid rich environments. A further benefit of carbon-supported catalyst is the low cost of the carbon support and the ability of recovering the metals from spent catalysts by simply burning off the carbon, rather than more expensive refining or recovery processes.

Preferred catalysts are based on nickel, on Ni—Cr or on Ni—Mn, or Ni—W, preferably supported on porous carbon. Although at least a bi-metallic catalyst is preferred, the process can use a mono-metallic catalyst of the group 10 metal, Ni based catalyst being preferred.

The catalyst can be prepared by classic precipitation methods, followed by drying and calcination. Before use, the catalyst is preferably reduced under hydrogen in situ, preferably at a temperature of about 150° C. to about 650° C. and a pressure of about 0.1 MPa to about 25 MPa (14.5-3625 psi).

Indeed we have found that while a range of transition metals are suitable for the first process step, nickel based catalysts were found to be effective with regard to performance and cost. Although nickel is known to be susceptible to leaching by carboxylic acids, Pienaar and Klerk (*Nickel Catalyst Stability towards Carboxylic Acids*, A. D. Pienaar and A. de Klerk, Ind. Eng. Chem. Res. 2008, 47, 4962-4965) found that leaching can be prevented by operation above the carboxylate decomposition temperature, which was found to be in the range 280-305° C. for the C2-C5 nickel carboxylates, as is the temperature range contemplated here.

Nickel-chromium catalysts containing nickel and reduced chromium oxides were found to be particularly effective as they substantially extend catalyst longevity compared with unalloyed nickel.

Within mass balance closures of greater than 99%, no coke was found to be deposited on the catalysts.

Hydroreforming Product

The liquid effluent from the hydroreforming step comprises a heavier aqueous phase and at least one lighter organic phase UBA. Analysis of the effluent shows no sign of polymerization. Depending on the catalyst, reaction time and reaction temperature, two organic phases might be formed, heavy UBA (HUBA) and light UBA (LUBA). Organic material (principally acetic acid and methanol) are dissolved in the aqueous phase. A gaseous phase containing mainly $CO_2$ and methane is produced as well.

Typically, in the first, hydroreforming, stage yields of the organic phase including the partially upgraded biooil on a biooil feed basis, are about 30 to about 50 mass %, preferably 40 to about 50 mass %, typically about 45 mass % together with about 30 to about 50 mass %, preferably about 35 to about 45 mass %, typically about 38 mass % of an aqueous phase, the latter containing less than about 20 mass % of organic materials (principally acetic acid and methanol). The remaining is the gas phase (mainly $CO_2$, $CH_4$ and CO) representing 5 to about 15 mass %, the total sum of organic, aqueous and gas phase being 100%. The conversion of the organic fraction of the biooil to the partially upgraded biooil is at least 70% by mass.

The aqueous phase contains essentially water being formed by hydrodeoxygenation and less than about 20% of organic materials dissolved therein. For pyrolysis biooils, the aqueous phase separated in the first reforming step typically contains about 10 mass % of acetic acid and a smaller amount of methanol. Preferably, the acetic acid and the methanol are recovered from the aqueous phase since they represent valuable by-products. Acetic acid can be recovered by various well known means such as distillation or evaporation, crystallization as a salt, e.g. of an alkaline earth, or solvent extraction e.g. by liquid ion exchangers. On account of its low boiling point and its lack of azeotropes with water, methanol is most simply recovered by distillation. Preferably, the acetic acid and the methanol together comprise at least 80% by mass of the organic components in the aqueous phase.

The organic phase UBA comprises partially upgraded biooil together with hydrocarbons. Generally, the organic phase UBA contains less than about 15 mass oxygen, preferably less than about 10 mass %. Preferably, the partially upgraded biooil contains less than about 25 mass % of oxygen. Thus, UBA is deoxygenated to a sufficient degree to render it miscible with typical refinery feeds at relatively high concentrations. UBA can blend freely with most hydrocarbon fuels in concentrations up at least 50% by mass. Furthermore, because the oxygen content is substantially reduced, any further hydrogen requirements during hydrotreatment/hydrocracking at a refinery are minimized. Moreover, UBA is stabilized so it can be hydrotreated/ hydrocracked in a refinery without the risk of solid formation.

Generally, the organic phase UBA contains less than about 2 mass % of water, generally less than about 1 mass %. Thus, UBA is essentially water free as the residual water forms the separate aqueous phase due of the presence of hydrocarbons in the reaction mixture which tend to expel water from the partially upgraded biooil phase so that its water content is as low possible. Preferably, the Total Acid Number (TAN) is less than about 100 and the higher heating value is greater than about 35 MJ/kg in the organic phase UBA.

The homogeneous mixture of hydrocarbons and partially upgraded biooil (UBA) with an overall water content less than about 2% by mass, preferably less than about 1% by mass, oxygen content less than about 25% by mass, preferably less than about 10% by mass and a Higher Heating Value greater than about 35 MJ/kg can be used as a hydrocracking, hydrotreating or catalytic cracking feedstock or as an industrial fuel.

Hydrotreatment/Hydrocracking

Since UBA still contains a significant amount of oxygenates it is not a pure hydrocarbon and needs further treatment to convert it to motor fuel grade products. Among the technologies available are hydrotreatment and/or hydrocracking. Commercial hydrotreating and/or hydrocracking catalysts are available that can steer the heavier components of UBA product towards naphtha or gasoline/jet fuel/diesel at somewhat higher severity conditions.

If the partially upgraded biooil was hydrotreated to provide a hydrocarbon liquid product that was recycled to the first stage, then all the carbon in the final hydrotreated product would constitute renewable carbon (i.e. be derived from biomass). This case, in which the hydroreforming stage is coupled to the hydrocracking/hydrotreating stage, is illustrated in FIG. 3A. It is also contemplated that other arrangements in which the first stage is coupled to such alternative sources of hydrocarbons, including fossil hydrocarbons, as may be envisaged by a person skilled in the art, are all within the scope of this invention.

The overall yield of UBB from bio-oil is typically close to 40 mass %. The yield of hydrocarbons in the second, hydrotreating, stage is higher than 80 mass %, typically about 83 mass % on a partially upgraded biooil basis. This yield does not take into account gas hydrocarbons nor valuables oxygenates formed during the hydroreforming and hydrotreatment/hydrocracking steps. Preferably, UBB contains less than about 1% oxygen and with a final boiling point of less than about 500° C. Preferably, the hydrogen consumption in the second stage is less than about 2% of the mass of the biooil fed.

Hydrotreatment

In the hydrotreatment step, the feedstock containing partially upgraded biooil, with or without the hydrocarbon liquid contained in the organic phase, is contacted with a heterogeneous catalyst and hydrogen at a temperature ranging between 250° C. and 450° C., preferably between 300° C. and 400° C., more preferably between 320° C. and 380° C. The pressure ranges between 2 MPa and 25 MPa (290-3625 psi), preferably between 5 MPa and 20 MPa (725-2900 psi). The hourly space velocity ranges between 0.1 $h^{-1}$ and 20 $h^{-1}$, preferably between 0.5 $h^{-1}$ and 5 $h^{-1}$.

In the hydrotreatment step at least one hydrotreatment catalyst bed comprising a hydro-dehydrogenating function and a support is used. A catalyst whose support is for example selected from the group made up of alumina, silica, silica-alumina, magnesia, clays and mixtures of at least two of these minerals is preferably used. This support can also contain other compounds and, for example, oxides selected from the group made up of boron oxide, zirconia, titanium oxide, phosphoric anhydride. A support consisting of alumina, more preferably of [eta], [delta] or [gamma] alumina is preferably used.

Said hydrogenising function of the catalyst is advantageously provided by a catalyst comprising at least one group 6 metal such as, for example, molybdenum and/or tungsten, preferably associated with at least one group 8 to 10 metal, for example nickel and/or cobalt. It is for example possible to use a catalyst comprising 0.5 to 10% by mass of nickel oxide (NiO), preferably 1 to 5% by mass of nickel oxide, and 1 to 30% by mass of molybdenum oxide ($MoO_3$), preferably 5 to 25% by mass of molybdenum oxide on an amorphous mineral support, the percentages being expressed in % by mass in relation to the total mass of catalyst. The total proportion of oxides of group 6 and group 8 to 10 metals in the catalyst used advantageously ranges between 5 and 40% by mass and preferably between 6 and 30% by mass in relation to the total mass of catalyst. The mass ratio expressed in metallic oxide between group 6 metal(s) and group 8 to 10 metal(s) advantageously ranges between 20 and 1, preferably between 10 and 2. Said catalyst used in the hydrotreatment step of the method according to the invention has to be advantageously characterized by a high hydrogenising power so as to orient as much as possible the reaction selectivity towards a hydrogenation keeping the number of carbon atoms of the chains, in order to maximize the yield in hydrocarbons falling within the distillation range of middle distillates. Maximizing the hydrogenising function also allows to limit the polymerization and/or condensation reactions leading to the formation of coke that would degrade the catalytic performance stability. Preferably, a NiMo, NiW or CoMo catalyst is used.

Said catalyst used in hydrotreatment step can also advantageously contain an element such as phosphorus and/or boron. This element can be introduced into the matrix or preferably deposited on the support. It is also possible to deposit silicon on the support, alone or with phosphorus and/or boron. The proportion by mass of oxide in said element is usually advantageously less than 20%, preferably less than 10% and it is usually advantageously at least 0.001%.

The metals of the catalysts used in the hydrotreatment step of the method according to the invention can be sulfur-containing metals or metallic phases. For maximum effectiveness these metal oxide catalysts are usually converted at least in part to metal sulfides. The metal oxide catalysts can be sulfided by any techniques known in the state of the art, for example in the reactor ("in-situ") or ex-situ by contacting the oxide catalyst at elevated temperatures with hydrogen sulfide, DMDS or a sulfur-containing oil or feedstock.

Since biomass normally contains only very little sulfur, the use of non-sulfided catalysts would avoid any possible sulfur contamination in the produced fuels. Therefore, other suitable metal oxide catalysts used in the hydrotreatment step are metallic phases obtained by reduction under hydrogen. Reduction is usually carried out at temperatures of about 150° C. to about 650° C. at a hydrogen pressure of about 0.1 to about 25 MPa (14.5-3625 psi).

A preferred metallic catalyst used in the hydrotreatment step of the method according to the invention comprises a noble transition metal selected from the group made up of Ni, Pd, Pt, Ru or Rh. The metal content ranges between 20% and 80% by mass, preferably between 55% and 65% by mass. The support of said catalyst is advantageously selected from the group made up of porous carbon, alumina, magnesium oxide and silica or mixture of at least both of them, and the support preferably consists of alumina.

The hydrotreatment can be carried out in an ebullated bed reactor, a fixed bed reactor, a moving bed reactor or a slurry reactor. A single catalyst or several different catalysts could be used simultaneously or successively in the case of a fixed bed reactor. This stage can be carried out industrially in one or more reactors with one or more catalyst beds. The reaction exotherm during hydrotreatment is limited by any method known to the person skilled in the art: liquid product recycle, quenching by the recycle hydrogen, etc.

Hydrocracking: Mild and High Pressure Hydrocracking

In the hydrocracking step, the feedstock containing partially upgraded biooil, with or without the hydrocarbon liquid contained in the organic phase, with or without any other feedstock from fossil origin, is contacted with a heterogeneous catalyst.

The upgrading of UBA comprises hydrocracking processes using hydrocracking catalysts, said processes encompassing the ranges of pressure and conversion from mild hydrocracking to high pressure hydrocracking. For simplicity, the term "hydrocracking" used herein encompasses mild and high pressure hydrocracking.

Mild Hydrocracking

Mild hydrocracking is understood to mean hydrocracking yielding moderate conversions, generally less than 50%, and operating at low pressure, generally between 2 MPa and 12 MPa. In a general manner, mild hydrocracking is usually performed under an absolute pressure of 2 to 12 MPa (290-1740 psi), often 2 to 10 MPa (290-1450 psi), and most often 4 to 9 MPa (580-1305 psi) or 3 to 7 MPa (435-1015 psi) at a temperature of between 250° C. and 480° C., and preferably between 350° C. and 450° C. The space velocity and the partial hydrogen pressure are selected based on the characteristics of the feedstock to be treated and the desired conversion. Most often, the space velocity is in a range that extends from 0.1 $h^{-1}$ to 20 $h^{-1}$, and preferably from about 0.2 $h^{-1}$ to about 5 $h^{-1}$. The total quantity of hydrogen mixed with the feedstock (including the chemical consumption and the recycled quantity) is usually such that the volume ratio hydrogen/hydrocarbon is between from about 100 to about 5000 Nm³/m³ and most often from 80 to 2000 Nm³/m³. Generally, it is at least 200 Nm³/m³ and preferably from 200 to 1500 Nm³/m³. The net conversion of products boiling below 375° C. is generally between 5 and 50% by mass, advantageously between 10 and 45% by mass.

The catalysts used in mild hydrocracking can be identical to those used in high pressure hydrocracking and are described in the following high pressure hydrocracking section of UBA. Before injection of the feed, the catalysts used in the process according to the present invention preferably undergo a preliminary sulfurization treatment to transform, at least partially, the oxide species into sulphide before they are contacted with the feedstock to be treated. This activation treatment by sulfurization is well known to the person skilled in the art and can be accomplished by any method already described in the literature either in-situ, that is in the reactor, or ex-situ.

High Pressure Hydrocracking

In the case of so called high pressure hydrocracking, the hydrocracking catalyst is contacted with the feed, in the presence of hydrogen at a temperature over 200° C., often between 250° C. and 480° C., advantageously between 320° C. and 450° C., preferably between 330° C. and 435° C., at a pressure between 2 MPa and 25 MPa (290-3625 psi), preferably between 5 MPa and 20 MPa (725-2900 psi), the hourly space velocity being comprised between 0.1 and 20 $h^{-1}$ and preferably between 0.1-6 $h^{-1}$, more preferably between 0.2-3 $h^{-1}$, and the quantity of hydrogen introduced is such that the volume ratio hydrogen/hydrocarbon Nm³/m³ is between 80 and 5000 Nm³/m³ and most often between 100 and 2000 Nm³/m³. These operating conditions used in the process according to the invention make it possible to attain conversions, of products with boiling points below 340° C., and preferably below 370° C., of more than 10% and even more preferably between 20 and 95%, more preferably between 50 and 95%.

The hydrocracking can be carried out in a fixed bed reactor or in a so-called entrained bed: moving bed reactor, ebullated bed reactor or a slurry reactor. A single catalyst or several different catalysts could be used simultaneously or successively in the case of a fixed bed reactor. The hydrocracking step can be done in one or more catalytic fixed or entrained beds or fixed and entrained bed, in one or more reactors, in a so-called single-stage or two-stage hydrocracking scheme such as described in US2007/0209968, with or without liquid recycling of the unconverted fraction, optionally in combination with a hydrorefining catalyst situated upstream of the catalyst of the present invention.

The hydrocracking step is generally preceded by a hydrorefining step to reduce potential harmful heteroatoms for the downstream hydrocracking catalyst(s). The hydrorefining catalyst comprises at least one amorphous support (generally alumina) and at least one metal or metal compound that has a hydro-dehydrogenating function (generally at least one metal selected from group 6 and groups 8 to 10, preferably at least one metal of group 6 and at least one non noble metal from groups 8 to 10). Preferably, the catalyst can also contain other elements such as phosphorus and/or boron and/or silicon, preferably phosphorus. The hydrorefining catalyst is contacted, in the presence of hydrogen at a temperature ranging between 250° C. and 450° C., preferably between 320° C. and 380° C., more preferably between 330° C. and 360° C., the pressure ranges between 2 MPa and 25 MPa (290-3625 psi), preferably between 5 MPa and 20 MPa (725-2900 psi). The hourly space velocity ranges between 0.1 $h^{-1}$ and 10 $h^{-1}$, preferably between 0.5 $h^{-1}$ and 5 $h^{-1}$, and the quantity of hydrogen introduced is such that the volume ratio hydrogen/hydrocarbon is most often between 100 and 2000 Nm³/m³.

The catalysts that are used in hydrocracking are all of the bifunctional type combining an acid function with a hydro-deshydrogenating function. The acid function is provided by substrates that generally have surface areas ranging from 150 to 800 m²/g and having a superficial acidity, such as halogenated aluminas (chlorinated or fluorinated in particular), aluminas, amorphous silica-aluminas and zeolites, or combinations thereof. The hydrogenating function is provided either by one or more metals of groups 8 to 10 of the periodic table, or by a combination of at least one metal of group 6 of the periodic table, and at least one metal of groups 8 to 10. The catalyst can be a catalyst that comprises metals of groups 8 to 10, for example nickel and/or cobalt, most often in combination with at least one metal of group 6, for example molybdenum and/or tungsten. It is possible, for example, to use a catalyst that comprises 0.5 to 10% by mass of nickel (expressed in terms of nickel oxide NiO) and from 1 to 30% by mass of molybdenum, preferably 5 to 20% by mass of molybdenum (expressed in terms of molybdenum oxide $MoO_3$) on an amorphous mineral substrate. The total content of metal oxides of groups 6 and groups 8 to 10 in the catalyst is generally between 5 and 40% by mass and preferably between 7 and 30% by mass. The ratio by mass (expressed on the basis of metal oxides) between metal (metals) of group 6 and metal (metals) of groups 8 to 10 is, in general, from about 20 to about 1, and most often from about 10 to about 2. In the case the catalyst comprises at least one metal of group 6 combined with at least one non noble metal of groups 8 to 10, the catalyst is preferably a sulfided catalyst.

The catalyst can also contain a promoter element such as phosphorus and/or boron. This element may have been introduced into the matrix or preferably have been deposited on the substrate. Silicon may also have been deposited on the substrate by itself or with phosphorus and/or boron. The catalysts preferably contain silicon that is deposited on a substrate such as alumina, optionally with phosphorus and/or boron deposited on the substrate and also containing at least one metal of groups 8 to 10 (Ni, Co) and at least one metal of group 6 (Mo, W). The concentration of said element is usually less than about 20% by mass (based on oxide) and most often less than about 10%. The boron trioxide ($B_2O_3$) concentration is usually from about 0 to about 10% by mass.

Other conventional catalysts comprise Y zeolite of the FAU type, a amorphous support (generally alumina) and at least one metal or metal compound that has a hydro-dehydrogenating function (generally at least one metal selected from group 6 and groups 8 to 10, preferably, at least one metal of group 6 and at least one non noble metal from groups 8 to 10).

Other suitable catalysts are so called composite catalysts described in US2007/0209968 comprising at least one metal or metal compound having a hydro-dehydrogenating function selected form group 6 and groups 8 to 10 and a support based on silica-alumina and at least one zeolite support.

Preferably, the hydrocracking catalyst comprises at least one group 8 to 10 metal selected from Ni and/or Co and at least one group 6 metal selected from Mo and/or W on a support of silica-alumina and/or zeolite.

Before injection of the feed, the catalysts used in the process according to the present invention preferably undergo a preliminary sulfurization treatment to transform, at least partially, the oxide species into sulphide before they are contacted with the feedstock to be treated. This activation treatment by sulfurization is well known to the person skilled in the art and can be accomplished by any method already described in the literature either in-situ, that is in the reactor, or ex-situ.

Co-Processing of UBA

Since UBA is deoxygenated by the hydroreforming step to a sufficient degree to render it miscible with typical refinery feeds at relatively high concentrations, UBA can blend freely with most hydrocarbon fuels in concentrations up to at least 50% by mass. Thus, the feedstock containing partially UBA upgraded biooil, with or without the hydrocarbon liquid contained in the organic phase can be coprocessed with a variety of other fossil feedstocks in existing hydrotreatment and/or hydrocracking step(s). The miscibility of UBA in fossil feedstocks allows its easy integration in already existing hydrotreatment and/or hydrocracking units, thus increasing the operability for refiners and decreasing both capital and operating costs to upgrade the biooils to fuels.

The fossil feedstock that can be co-treated generally contains at least 20 percent by volume above 250° C. and often at least 50 percent by volume of compounds boiling above 350° C. For example the feedstock can be atmospheric distillates or vacuum distillates, for example distillates derived from direct distillation of crude or conversion units such as FCC, coker or visbreaking, and also feedstocks obtained from aromatic extraction units from base lubricating oils or derived from solvent dewaxing of base lubricating oils, or distillates derived from processes of residue hydrotreatment and/or hydroconversion from fixed-bed or moving bed or ebullated-bed or slurry bed hydroconversion of atmospheric residues and/or vacuum residues and/or deasphalted oils obtained from any solvent deasphalting process using light solvents, or else the feedstock can be a deasphalted oil, or any mixture of the feedstocks previously cited. The above list is not limitative. The content of n-C7 insolubles is generally less than 5000 ppm, preferably less than 1000 ppm, and more preferably less than 200 ppm.

The resulting liquid product from either hydrotreatment and/or hydrocracking, designated UBB, generally contains less than about 1 mass % oxygen and less than about 0.1 mass % of water. The Total Acid Number of UBB is usually less than 1 mg KOH/g. The "Total Acid Number" (TAN) is expressed in mg KOH/g oil. It is the amount of potassium hydroxide in milligrams that is needed to neutralize the acids in one gram of oil. There are standard methods for determining the acid number, such as ASTM D 974 and DIN 51558 (for mineral oils, biodiesel), or specifically for biodiesel using the European Standard EN 14104 and ASTM D664, both widely utilized worldwide.

The higher heating value (HHV) of UBB is of about 45 MJ/kg which is comparable to that of diesel. The final boiling point of UBB, measured by simulated distillation by gas chromatography, such as according to ASTM D2887 method, is less than about 500° C., preferably less than 450° C.

UBB is preferably at least partly recycled to the hydroreforming stage as hydrocarbon liquid so that all the carbon in the final hydrotreated product constitutes renewable carbon (i.e. derived from biomass).

Further Upgrading of UBB

UBB can be further upgraded if needed to obtain transportation fuel such as diesel/kerosene or jet fuel respecting specifications. The upgrading of UBB comprises hydrocracking processes using hydrocracking catalysts under high pressure hydrocracking conditions (in terms of conversion and pressure).

The operating conditions, catalysts used and reactor configurations for high pressure hydrocracking of UBB are identical to those described for the upgrading of the feedstock containing partially upgraded biooil, with (UBA) or without the hydrocarbon liquid contained in the organic phase from the hydroreforming step.

Like UBA, UBB can be co-processed with a variety of other feedstock derived from petroleum. The fossil feedstock that can be co-treated are identical to those described for the upgrading of the feedstock containing partially upgraded biooil, with (UBA) or without the hydrocarbon liquid.

The scope of the invention may be understood by means of the examples described in detail below. While the invention has been described with what are presently considered the preferred embodiments, it is to be understood that the invention is not limited to the disclosed embodiments, but is intended to cover various modifications and equivalent arrangements included within the scope of the appended claims.

EXAMPLES

The following are specific examples of the invention; however, there is no intention to be bound thereto.

Equipment

Figure 2:
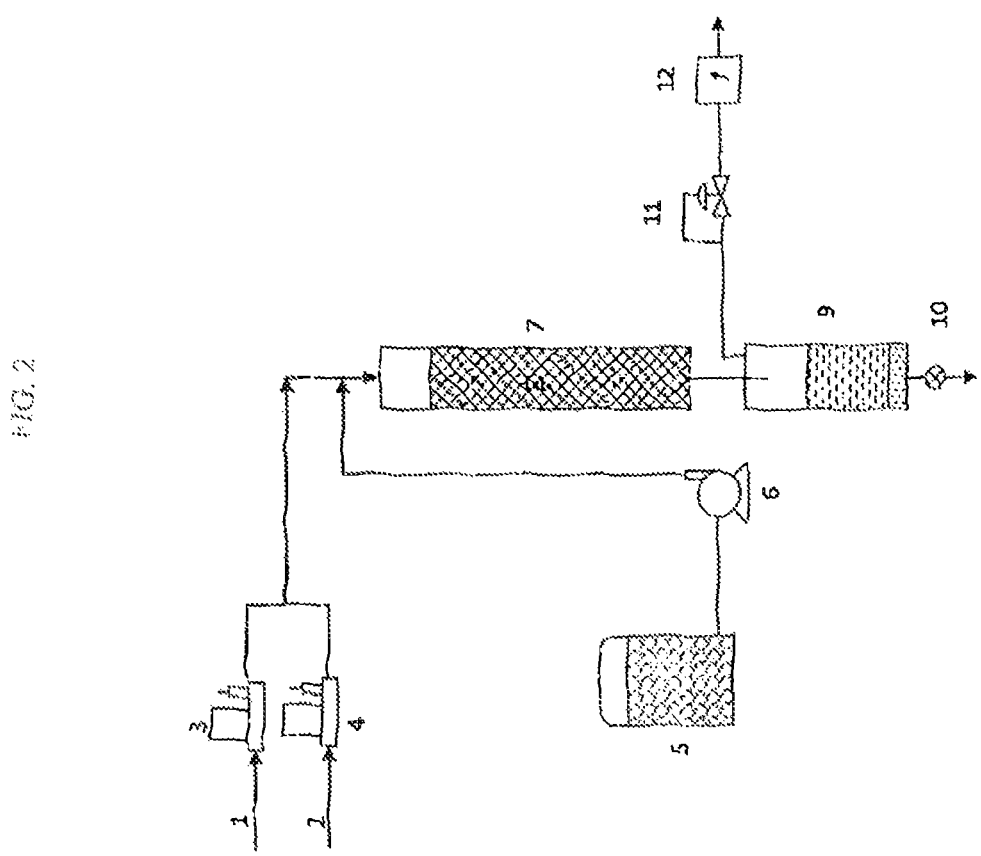
FIG. 2 illustrates the experimental arrangement used herein for Step 2 in continuous mode.

The following experimental examples were carried out in the apparatus illustrated in FIGS. 1 and 2. FIG. 1 depicts the experimental setup for the first stage of the process. In continuous mode of operation, hydrogen, 1, and nitrogen, 2, for use as a tracer, were introduced into a Parr autoclave reactor, 9, through mass flow controllers 3 and 4 respectively while biooil, 5, and hydrocarbon, 6, were introduced into the reactor through liquid metering pumps 7 and 8 respectively. The reactor was stirred by magnetic stirrer 10, while effluent gases exhausted through tubular reflux condenser 11, back pressure regulator 12, and gas volume meter 13. The liquid effluent, UBA, was removed through a sintered metal filter 14, liquid cooler 15, needle valve 16, to the receiver 17, where phase separation occurred. In batch mode of operation valves 18, 19, and 20 were closed after the reactor was charged with liquid and gaseous reactants. The system could also be operated in a semi-continuous liquid mode where gases were in constant flow but the liquid product was manually discharged intermittently through needle valve 20.

Continuous hydrotreating experiments for the second stage were carried out in the experimental setup illustrated in FIG. 2. Hydrogen 1, and nitrogen for use as a tracer, 2, were introduced into a tubular reactor 7, which contained a packed bed of catalyst, 8. Partially upgraded biooil 5, was introduced through metering pump 6, while the liquid effluent, UBB, was removed via needle valve 10, collected in vessel 9 and the gaseous effluent discharged through back pressure controller 11 and gas meter 12.

Biooil Properties

Most of the experiments were conducted with a biooil derived by fast pyrolysis of hardwood mixtures. Its water content was usually between 25 to 30% by mass. A typical analysis of this biooil yielded the following data in table 1:

TABLE 1

Biooil analysis

| | |
|---|---|
| Density at 20° C., g/cm³ | 1.19 |
| Dynamic Viscosity at 20° C., cP | 68.8 |
| Surface Tension at 20° C., mN/m | 38.5 |
| pH | 2.8 |
| Higher Heating Value, MJ/kg [a] | 16.6 |
| Lower Heating Value, MJ/kg [b] | 14.9 |
| Water content, Mass % | 25.1 |
| Pyrolytic Lignin, Mass % | 21.0 |
| Carbon | 41.8 |
| Hydrogen | 7.6 |
| Nitrogen | <1 |
| Oxygen (by difference) | 50.6 |
| Some Water-Soluble Organic Components, Mass % | |
| Hydroxyacetaldehyde | 7.0 |
| Levoglucosan | 5.8 |
| Acetic acid | 9.8 |
| Acetol | 2.3 |

[a] Higher Heating Value is measured by Bomb Calorimetry,
[b] Lower Heating Value is calculated by following equation: LHV (J/g) = HHV (J/g) − 218.13 * H % (wt %).

The surface and interfacial tensions of biooil were measured with a Fisher 21 Tensiomat DuNouy ring surface tension meter. The interfacial tension between biooil and biooil saturated UBA was 8.1 mN/m at 20° C., a low value indicating that the free energy required for efficient dispersal of the former in the latter is small, a fact facilitative of the present invention in so far as it implies good dispersibility biooil under the preferred conditions.

Method of Catalyst Preparation

Carbon was found to be a particularly suitable support for the catalyst compared to typical metal oxide supports like silica or alumina, which tend to hydrolyse and deteriorate in water and acid rich environments at elevated temperatures. The specific examples discussed herein were some carried out with carbon supported catalysts prepared in the exemplary manner described in Example 1.

Example 1: Catalyst Preparation

A catalyst designated as 10Ni-5Cr/AC containing 10% Ni and 5% Cr on Activated Carbon was prepared by the following procedure. Nickel nitrate hexahydrate, Ni(NO3) 2.6H2O, (5 g) and Chromium nitrate monohydrate, Cr(NO3) 3.1H2O, (3.8 g) were dissolved in a small amount of deionised water (~15 g). The support was Norit RX3 Extra Activated Carbon (surface area about 1400 cm2/g, ball-pan hardness 99 and pore volume about 1 cm3/g with about 75% of its porosity in meso- and macropores). The Activated Carbon pellets were crushed to a powder with particle diameter about 1 mm. A portion of the prepared solution was absorbed into the powdered carbon support until its porosity became saturated. The saturated carbon was then dried at ~70° C. in air, after which the remaining solution was absorbed onto the carbon which was again dried at ~70° C. The resulting impregnated catalyst material was calcined in air at ~300° C. for ~3 hrs. Finally, before use, it was reduced under H2 at 330° C. in situ.

Example 2: Batch Hydroreforming with Butanol as Bridging Solvent

This example illustrates the use of n-butanol as a bridging solvent for dispersing biooil in a hydrocarbon liquid. Both biooil and hydrocarbons have high solubilities in butanol. 10 g of a 10Ni/AC catalyst, prepared as in Example 1, were placed in the autoclave reactor and reduced under a trickle flow of hydrogen at 330° C. for 3 hours. The reactor was cooled and 101.0 g of biooil, 30.1 g of n-butanol and 21.0 g of xylenes were added to it. The autoclave was sealed, pressurized to 900 psia (6.2 MPa) with 10.5 L NTP of H2 and then gradually heated with stirring to 250° C. over a period of about 2.5 hrs. The reactor was maintained at 250° C. for a further 2 hrs after which it was cooled. Since the pressure had risen to nearly 2000 psia (13.8 MPa) by this time, the reactor was quickly cooled to room temperature, causing the pressure to fall to 330 psia (2.3 MPa). The product gas, a total of 3.8 L, was vented and analyzed. Gas chromatographic analysis indicated that it contained 59.10% of H2, 35.25% CO2, 4.88% CO and 0.77% CH4 by volume.

Inspection of the reactor contents showed no signs of biooil polymerization or coking. The catalyst was filtered off from the liquid product which separated into 93.6 g of an upper homogeneous organic liquid oil phase with viscosity of about 12 cP at 20° C. and 42.8 g of a bottom aqueous phase. No tar deposits were observed in the reactor. The organic liquid contained 5.31% (4.97 g) and the aqueous phase 79.9% (34.19 g) of water, determined by Karl-Fischer titration. A further 1.5 g of water were held up on the catalyst (determined by Karl-Fischer titration of a suspension of the catalyst in methanol). The catalyst was thoroughly washed in methanol and dried at 70° C. It showed no weight gain within experimental error, suggesting little or no coke formation.

The reactor was then flushed with nitrogen and re-pressurized with hydrogen to 300 psia (2.1 MPa) after which it was rapidly heated to 317° C., where the pressure rose to about 1800 psia (12.4 MPa), and maintained at this temperature for a further 2 hrs. After quenching to room temperature the pressure fell to 250 psia (1.7 MPa).

The total volume of gaseous product was about 3.5 L NTP. Its composition was 45.98% of hydrogen, 31.23% CO2, 14.37% CO, 7.6% CH4 and 1.26% C2+ hydrocarbons, by volume.

A material balance was carried out on butanol as it may be anticipated that some of it may have been reacted and consumed. It was found that the oil phase contained 18.7 g of butanol and 5.0 g of butyl acetate while the aqueous phase contained 1.6 g of butanol giving an overall recovery of butanol equivalents of about 78.1%, confirming that some butanol had indeed been consumed.

92.2 g of the organic liquid were distilled at about 140° C. to produce 46 g of a butanol and xylene rich distillate and 46 g of a residual partially upgraded biooil (PUB) containing 1.75 g butanol, 3.67 g xylenes and 1.14 g of butyl acetate. This indicates that the yield of PUB is of the order of at least 40% of the initial biooil and that the bulk of it boils at greater than 140° C.

Liquid chromatographic analysis of the aqueous phase indicated that, besides butanol, it contained 1.58 g methanol and 2.35 g acetic acid.

The overall net consumption of hydrogen was 10.14 L NTP (0.91 g) which corresponds to about 0.9 mass % based on biooil reacted. However since it is seems likely that some hydrogen was generated from butanol this is probably an underestimate. Likewise, there was a net production of 1.33 L NTP of CO2 corresponding to 4.8% based on biooil.

This result teaches that since hydrocarbons and biooils both have high solubility in butanol, the expectation that it is a good bridging solvent for dispersion of biooil in hydrocarbons, supporting the principle that coke free processing of biooil in a hydrocarbon is possible with the aid of a dispersant, in this case an alkanol co-solvent.

a. Although loss of butanol is not so large, butanol is relatively expensive so it is desirable to find a cheaper dispersant.
b. These data suggest that most of the hydrogen is absorbed at a relatively low temperature (~250° C.) and consequently that any internal reforming of biooil to hydrogen preferentially takes place at the higher temperature (~320° C.).

Example 3: Batch Hydroreforming Using Partially Upgraded Biooil as Bridging Solvent The partially upgraded biooil (PUB) distillation residue produced in Example 2 is partially deoxygenated compared to raw biooil and therefore may be expected to be more hydrophobic. It was hypothesized that it might itself serve as a bridging solvent (dispersing agent). Consequently a batch experiment was carried out in a similar fashion to Example 2, but in which the reactants were 25 g of the PUB, 25 g of biooil, 12.4 g of xylenes and 5 g of 10Ni/AC catalyst. The autoclave was pressurized with hydrogen to 400 psia (2.7 MPa) and rapidly heated to 320° C. where it was maintained for 3 hrs, during which time the maximum pressure reached was 1820 psia (12.5 MPa).

After cooling, the liquid product separated into 38.1 g of a lighter organic oil phase and 10.4 g of a denser aqueous phase. The aqueous phase had a water content of 80.81 mass % and contained 1.96 g of acetic acid and 0.05 g of methanol. The oil phase had a water content of 1.71% and a dynamic viscosity of 13.1 cP at 20° C.

3.57 L of hydrogen were consumed and 1.32 L of $CO_2$ produced corresponding to a hydrogen consumption of 1.28 g H2/g biooil.

This result confirms that partially upgraded biooil can indeed serve as a bridging solvent so that a continuous process can be envisaged in which biooil and a hydrocarbon are fed to a mixed reactor containing partially upgraded biooil and hydrocarbons.

The mixture of partially upgraded biooil and hydrocarbons, xylenes in this instance, designated as UBA, was estimated to contain about 30.5 mass % of xylenes.

Example 4: Batch Hydroreforming Using a Lower Biooil to Xylene Ratio

The biooil to xylene ratio was then decreased from the value of about 2 in Example 3 to about 1.5 by reacting 38.0 g of biooil with 18.3 g of the whole organic phase liquid product from Example 3 (approximately containing 8 g xylene) together with an additional 17.2 g of xylene, using 5 g of 10Ni/AC catalyst at 320° C. for 4 hrs.

49.3 g of an organic oil containing 1.44% water were obtained. Its viscosity was 10.9 cP at 20° C. its Higher Heating Value (HHV) was 42.04 MJ/kg as determined by bomb calorimetry. (For comparison the HHV of xylenes was measured as 42.50 MJ/kg.)

Hydrogen consumption was also significantly decreased to about 1.1 mass % of raw biooil.

This example also suggests that the water content of the oil phase can be minimized by increasing the ratio of hydrocarbon to biooil in the reaction mixture.

Example 5: Batch Hydroreforming Using Surfactants as a Dispersing Agent

This example illustrates the use of a surfactant as a dispersion aid for biooil in a hydrocarbon fluid. The polyethlyene glycol (PEG) alkyd resin surfactant Atlox™ 4914, (Uniqema), was chosen for illustration since it has already been shown to be able to emulsify biooil in diesel (*Development of emulsions from biomass pyrolysis liquid and diesel and their use in engines—Part 2: tests in diesel engines*, D. Chiaramonti et al, Biomass and Bioenergy 25, 101-111, (2003)). 27.0 g biooil were reacted in 54 g of a No. 2 diesel containing 5% Atlox in a batch reaction. The reactor was pressurized to 550 psia (3.8 MPa) with hydrogen and heated rapidly to 330° C. where it was maintained for 4 hrs.

On cooling, 64.4 g of a lighter organic liquid phase that had a density of only 0.860 g/cm$^3$ and water content of only 0.2%, separated from an 11.3 g of an aqueous phase containing 80% water and 20% total organics including 1.29 g acetic acid and 0.81 g methanol.

The result supports the proposition that the efficacy of the inventive process relates more to the degree of physical dispersion of biooil rather than to any specific chemical effect. It also confirms that the role of the hydrocarbon does not depend on a hydrogen donor effect, since xylene is not a known H-donor. For further confirmation the experiment was rerun with the known hydrogen donor decalin as the hydrocarbon and the results were found to be similar in all respects.

Since at start-up there would be no UBA in the reactor to assist dispersion of biooil this finding therefore provides a simple way to initialize the process.

Example 6: Batch Mode Hydrotreating of UBA

This example illustrates that it is possible to convert the partially upgraded biooil to hydrocarbons by hydrotreating with conventional hydrotreating catalysts.

An experiment was carried out batchwise in the apparatus of FIG. 1. A nickel-molybdenum on alumina catalyst, TK-559 (Haldor Topsoe) was used; it was crushed and sulfided according to the manufacturer's recommended procedure. 33.0 g of the distillation residues of partially upgraded biooil, obtained in a similar manner to that described in Example 2, were mixed with 4.0 g of xylenes and 5 g of sulfided and reduced catalyst. The reactor was pressurized with 14.0 L NTP with hydrogen to 1050 psia (7.2 MPA), heated rapidly to 350° C. and maintained at that temperature for 4 hrs before quenching; the maximum pressure attained was about 1850 psia (12.8 MPa).

On cooling the pressure fell to about 450 psia (3.1 MPa); the estimated hydrogen consumption was 8.51 L while 0.71 L of $CO_2$ was produced. There was no visible evidence of coke or solids formation. The liquid product separated into 25.5 g of a light oil phase containing 0.5 mass % water and 3.5 g of an aqueous phase containing 90.0 mass % of water.

The HHV of the oil phase was measured as 46.50 MJ/kg by bomb calorimetry. This result confirms that partially upgraded biooil can be successfully hydrotreated with conventional catalysts.

By repeating the cycle of using the hydrotreated oil product in place of xylene in the production of partially upgraded biooil, the concentration of the original xylene in the final UBA product can be reduced to zero asymptotically so that the final composition of UBB will approach 100% renewable carbon.

Example 7: Trickle Bed Hydrotreating of UBA

In this example UBB was produced in continuous downflow (trickle) mode in the tubular reactor setup illustrated in FIG. 2. The catalyst bed consisted of a mixture of 12 g of crushed extrudates Co—Mo/Al2O3 catalyst (TK-558 BRIM™ Topsoe) which was pre-sulfided and reduced, together with 28 g of silica sand. The feed consisted of UBA, to which was added a small amount of dimethyl disulfide (DMDS) to maintain sulfidation of the catalyst, and was pumped into the reactor at the rate of 0.6 cm$^3$/min, together with a flow of about 100 cm$^3$ NTP/min of hydrogen gas, continuously over a period of about 2 days.

The rate of the reaction is characterized by the Weight Hourly Space Velocity (WHSV) which is defined here as the ratio of the mass of partially upgraded biooil, exclusive of the hydrocarbon content of the UBA feed, fed per hour to the mass of catalyst. Assuming the feed contained 60% of partially upgraded biooil, the corresponding Weight Hourly Space Velocity (WHSV) was about 2 hr$^{-1}$. The temperature was held at 325° C. and the pressure at 1900 psia (13.1 MPa).

The product was a clear, yellow oil designated as UBB. It was estimated to contain about 7-9% of xylenes. Some of its overall properties were determined as follows (table 2):

TABLE 2

Physical and chemical properties of UBB

| | |
|---|---|
| Density (g/cm$^3$) | 0.84 |
| TAN (mg KOH/g) | 0.5 |
| Final Boiling Point (° C.) | ~450 |
| Water (mass %) | ~0 |
| Carbon (mass %) | 89 |
| Hydrogen (mass %) | 11 |
| Sulfur (mass %) | 0.0001 |
| Nitrogen (mass %) | <0.01 |
| Oxygen* (mass %) | ~0 |
| Paraffines (mass %) | 15.7 |
| Naphtenes (mass %) | 24.9 |
| Aromatics (mass %) | 48.3 |
| Olefins (mass %) | 2.2 |
| C13$^+$(mass %) | 8.9 |

*by difference

In addition, a Research Octane Number (RON) of about 97 was calculated from the compositional data in the table above, though it must be emphasized that this is a very crude estimate as the calculations used were based on a method intended for petroleum based gasoline.

Figure 5:
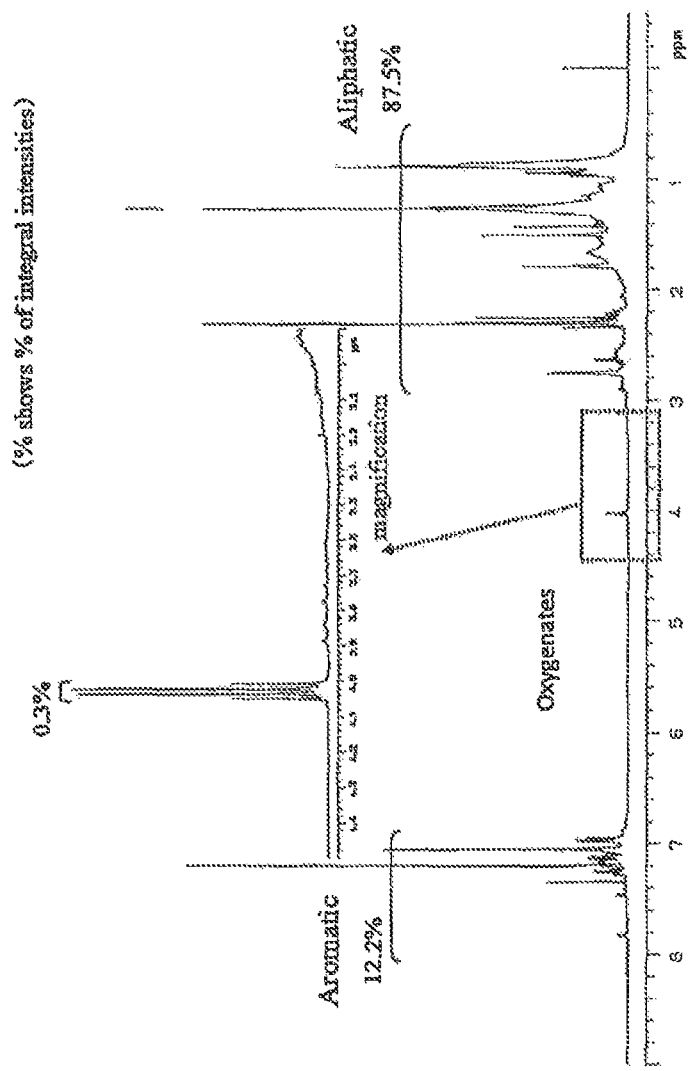
FIG. 5 shows the $^1$H NMR spectrum of the upgraded biooil product, UBB.
Figure 6:
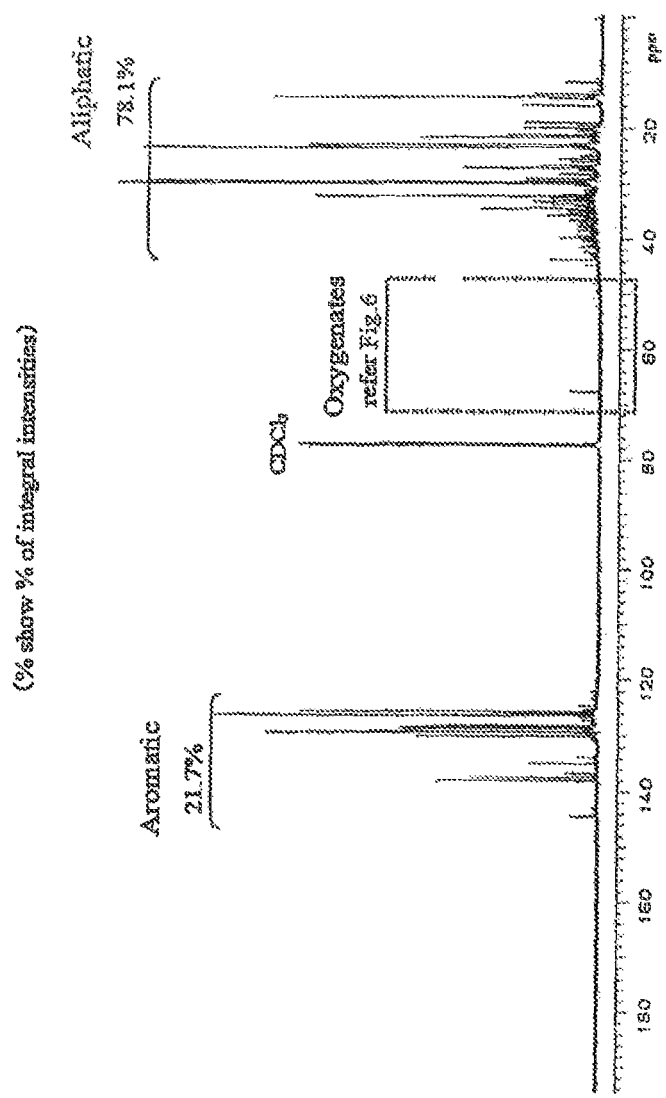
FIG. 6 shows the $^{13}$C NMR spectrum of the upgraded biooil product, UBB.

A proton NMR spectrum of the product (UBB) is displayed in FIG. 5 and a $^{13}$C NMR spectrum in FIG. 6.

Example 8: Example of Semi-Continuous UBA Production

This example illustrates the semi-continuous production of UBA with recycle of UBB in the reactor configuration of FIG. 1 where the autoclave is operated as a Continuous Stirred Tank Reactor (CSTR). Hydrogen gas (1), which was admitted through the mass flow controller (3), was in continuous flow but a fixed amount of biooil and hydrocarbon (UBB) was pumped in intermittently. After each addition of biooil a corresponding amount of product (UBA) was manually released through needle valve (16) into the collector vessel (17) in such amounts as to maintain the liquid volume in the reactor approximately constant.

In order to minimize loss of hydrocarbon from the reactor, the hydrocarbon recycle was taken as the >140° C. distillation cut of a UBB product that had been prepared in the manner of Example 7. 10 g of a Ni—Cr/AC catalyst prepared as in Example 1 was slurried in about 50 g of UBB and placed in the reactor where it was reduced at 330° C. in H$_2$ for about 3 hrs.

The reactor was then charged initially with 100 g of a mixture of biooil (BCO), UBA and UBB in the ratios 2:2:1, respectively. (Assuming that UBA consists of ~50% of partially upgraded biooil (PUB) and 50% of the hydrocarbon UBB, the effective ratios BCO:PUB:UBB are 2:1:2.)

Rather than feed the biooil neat, it was fed as a 1:1 mixture with UBA (S. G. (specific gravity)~1) in order to minimize plugging of the feed tube due to biooil polymerization therein. 25 g of this feed mixture was pumped into the reactor at 45 min. intervals together with 6.25 g of UBB, which was pumped in separately. Hydrogen gas was continuously metered in at a rate of 140 cm$^3$ NTP/min while the reactor was maintained at a pressure of 1850 psia (12.8 MPa) and a temperature of 330° C. At the same time, about 24 g of liquid product, including about 5 g of an aqueous phase was manually removed.

At the end of the first day 175 g of the organic liquid product UBA and 38 g of an aqueous phase of pH 3.1 had been collected. The aqueous phase contained about 8% of acetic acid.

Some physical properties of the UBA were (table 3):

TABLE 3

Physical properties of UBA

| | |
|---|---|
| Density (g/cm$^3$) | 0.84 |
| TAN (mg KOH/g) | 20.3 |
| Water content (mass %) | 1.1 |

The average WHSV was about 1.3 hr$^{-1}$ based on raw biooil fed. The gas phase was also analyzed at regular intervals during the run. A typical volumetric compositional analysis was (table 4):

TABLE 4

Volumetric compositional analysis of the gas phase

| Gas | H2 | CO2 | CO | CH4 | C2+ |
|---|---|---|---|---|---|
| Vol % | 88.9 | 6.8 | 2.4 | 1.5 | 0.4 |

While still sealed, the reactor was allowed to cool to room temperature under hydrogen overnight. The next day it was heated up to the operating temperature after which the biooil feed was restarted. The products, UBA, aqueous phase and gas, were essentially the same as before and this sequence was repeated on subsequent days.

On the 6'th day, after a total of 1.02 kg of UBA had been produced, corresponding to about 2.3 kg of raw biooil, it was noticed that the UBA phase slowly separated into 80% of a lighter phase, LUBA, and 20% g of a heavier phase, HUBA with the properties listed in the table below (table 5):

TABLE 5

Physical properties of LUBA and HUBA

| | LUBA | HUBA |
|---|---|---|
| Density (g/cm3) | 0.90 | 0.97 |
| TAN (mg KOH/g) | 22.2 | 55.0 |
| Water content (mass %) | 1.20 | 4.66 |

At this point the run was terminated, though it should be borne in mind that the daily temperature cycling of the catalyst may not have been conducive to its stability and longevity.

After repeated runs like that described in Examples 6 and 7, in which xylenes used in the first step are progressively replaced by hydrotreated biooil (UBB), the level of xylene in the final product UBB was brought down to about 6%. The UBA samples that were subjected to more detailed analyses were mainly produced in a tubular reactor as described in Example 8.

Figure 7:
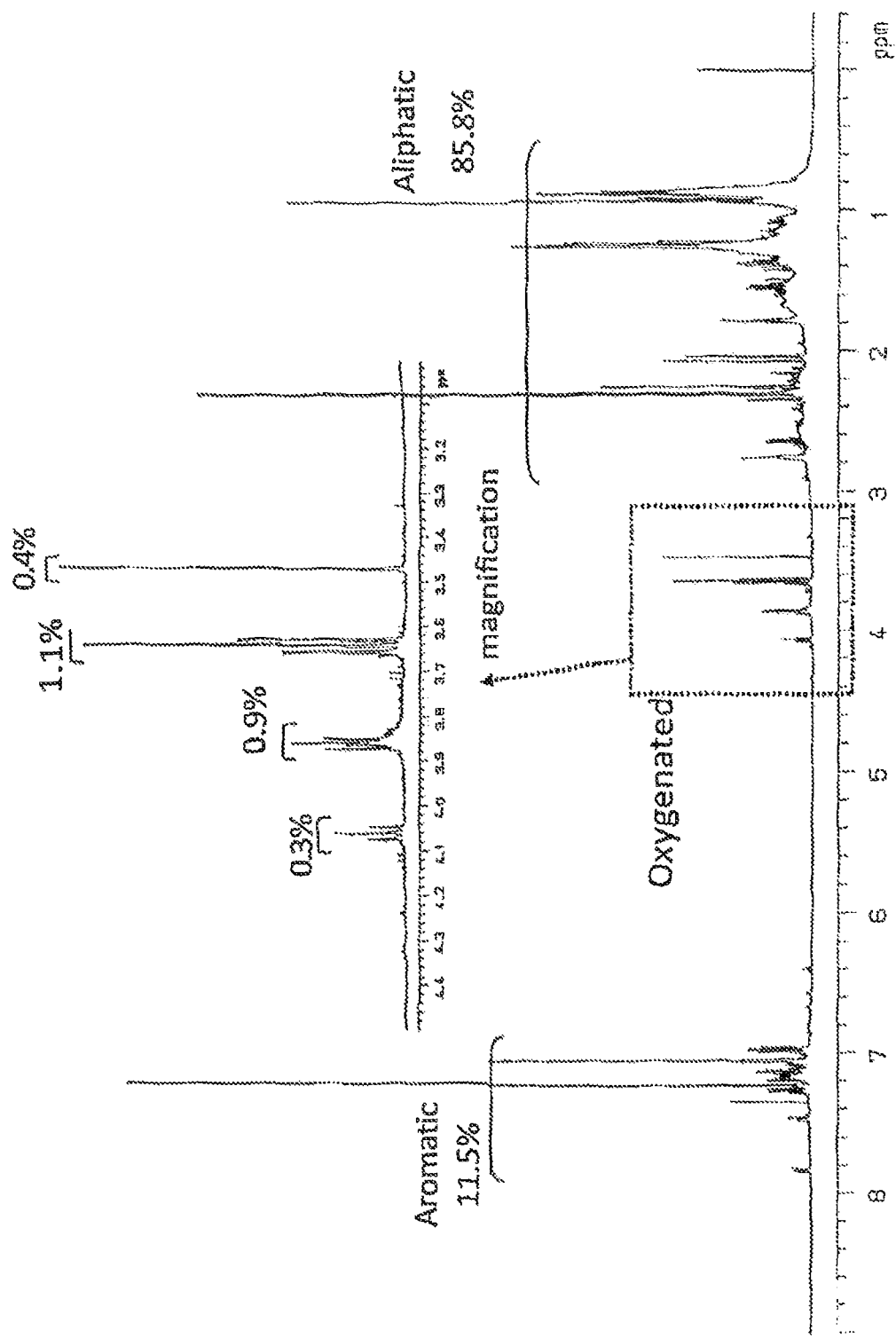
FIG. 7 shows the $^1$H NMR spectrum of the partially upgraded biooil product, UBA.
Figure 8:
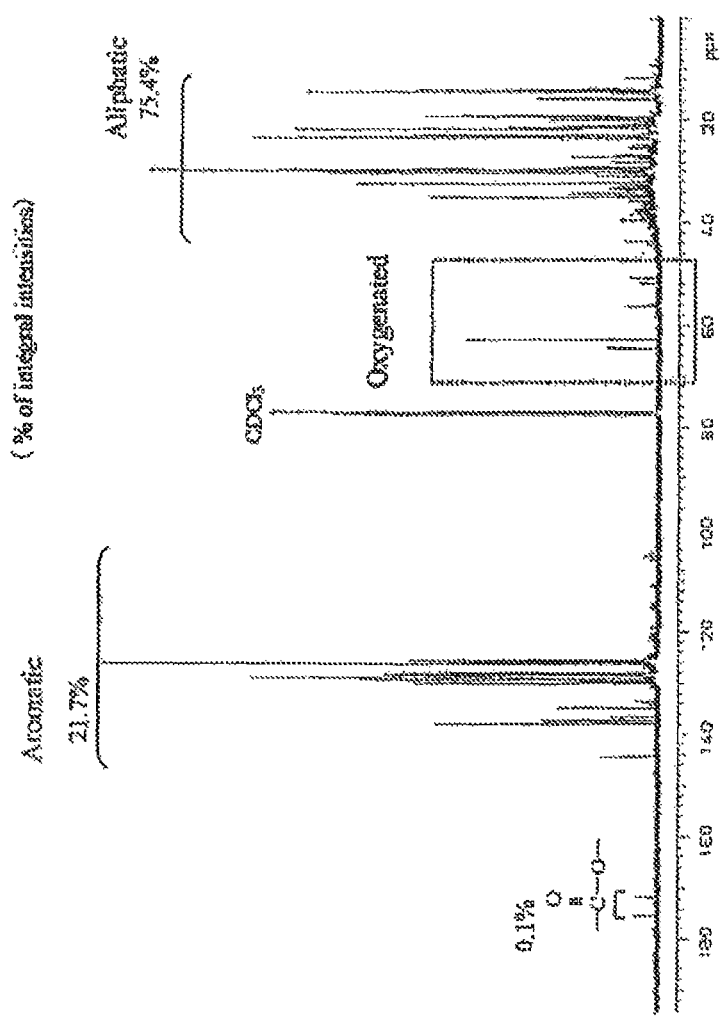
FIG. 8 shows the $^{13}$C NMR spectrum of the partially upgraded biooil product, UBB.

A proton NMR spectrum of the product (UBA) is displayed in FIG. 7 and a $^{13}$C NMR spectrum in FIG. 8. The following table (table 6) compares the elemental compositions in mass % of UBA and UBB.

TABLE 6

Elemental composition in mass % of UBA and UBB

|   | UBA   | UBB    |
|---|-------|--------|
| C | 81.8  | 87.7   |
| H | 10.9  | 12.2   |
| O | 7.2   | 0.1    |
| N | 0.06  | <0.01  |
| S | 0.031 | 0.0001 |

Example 9: Comparison of Ni with NiCr Catalysts for UBA Production

This example illustrates the performance of a 10Ni/AC catalyst in comparison with the 10Ni-5Cr/AC catalyst of Example 8. The experiment was carried out in a similar manner to Example 8, except that the ratios of biooil, UBA and UBB fed were 2:1:1 instead of 2:2:1.

The operating conditions and the products were otherwise similar to Example 8. A two-phase UBA now appeared after only 3 days of operation. A single phase, homogenous UBA was restored by decreasing the WHSV from 1.4 to 0.8 hr-1.

Now in Example 8, the ratio Biooil/PUB was estimated to be ≈2 and Biooil/UBB≈1.3 but in the present example Biooil/PUB≈4 and Biooil/UBB≈1. It is not unexpected that the higher ratio of biooil to partially upgraded biooil is more unfavourable since the latter is presumed to function as the dispersing agent. Consequently, the catalysts were compared under similar ratios: 10 g of a 10Ni-5Cr/AC catalyst was used with a biooil:UBA:UBB feed ratio of 2:1:1 and reaction temperature of 330° C. It now took 9 days (equivalent to 68 hours on line) of operation before the UBA product separated into LUBA and HUBA phases that had the following properties (table 7):

TABLE 7

Physical properties of LUBA and HUBA

|                    | LUBA | HUBA |
|--------------------|------|------|
| Density (g/cm3)    | 0.88 | 0.96 |
| TAN (mg KOH/g)     | 22.0 | 62.0 |
| Water content (mass %) | 1.04 | 4.71 |
| HHV (MJ/kg)        | 43.2 | 34.5 |

As before, acetic acid was 7.8% of the aqueous phase.

We conclude that decorating Ni particles with reduced chromium oxides substantially enhances catalyst lifetime under the conditions of the process.

Example 10: Trickle Bed Hydrotreating of UBA to UBB with Non-Sulfided Catalyst

Since biomass normally contains only a very little sulfur, the use of a non-sulfided catalyst was explored in order to examine the feasibility of avoiding the use of sulfur altogether. A NiMo/Al2O3 hydrotreating catalyst TK-559 BRIM (Haldor Topsoe) containing 2% Ni and 10% Mo was chosen. The experimental arrangement was similar manner to Example 7 except that the catalyst bed contained 6 g of catalyst diluted with 36 g of sand and the catalyst was only reduced at 350° C. and not sulfided as well.

Various UBA samples, including LUBA and HUBA, were pumped over the catalyst at space velocities varying in the range 2.4-4.0 hr$^{-1}$ (WHSV) and temperatures in the range 325-350° C. while the pressure was held constant at 1900 psia (13.1 MPa) and the hydrogen flow rate was fixed at 150 cm$^3$ NTP min-1. The densities of the UBB products ranged from 0.82-0.84 g/cm$^3$ while their water contents varied from <0.01-0.14 mass %. The mean molar percentage composition of the gaseous effluent was H2 (79.8%), CO2 (2.0%), CO (1.0%), CH4 (12.9%) and C2+(4.3%). Hydrogen consumption averaged 1.52 mass % of the UBA feed.

In all, over a period of several days 1 kg of UBA was treated by the 6 g of catalyst. We conclude that the results indicate that UBA can be stably hydrotreated with reduced, non-sulfided catalysts so that by recycling UBB very low sulfur fuels can be obtained.

Example 11: Molecular Weight Distributions of UBA and UBB

Figure 4:
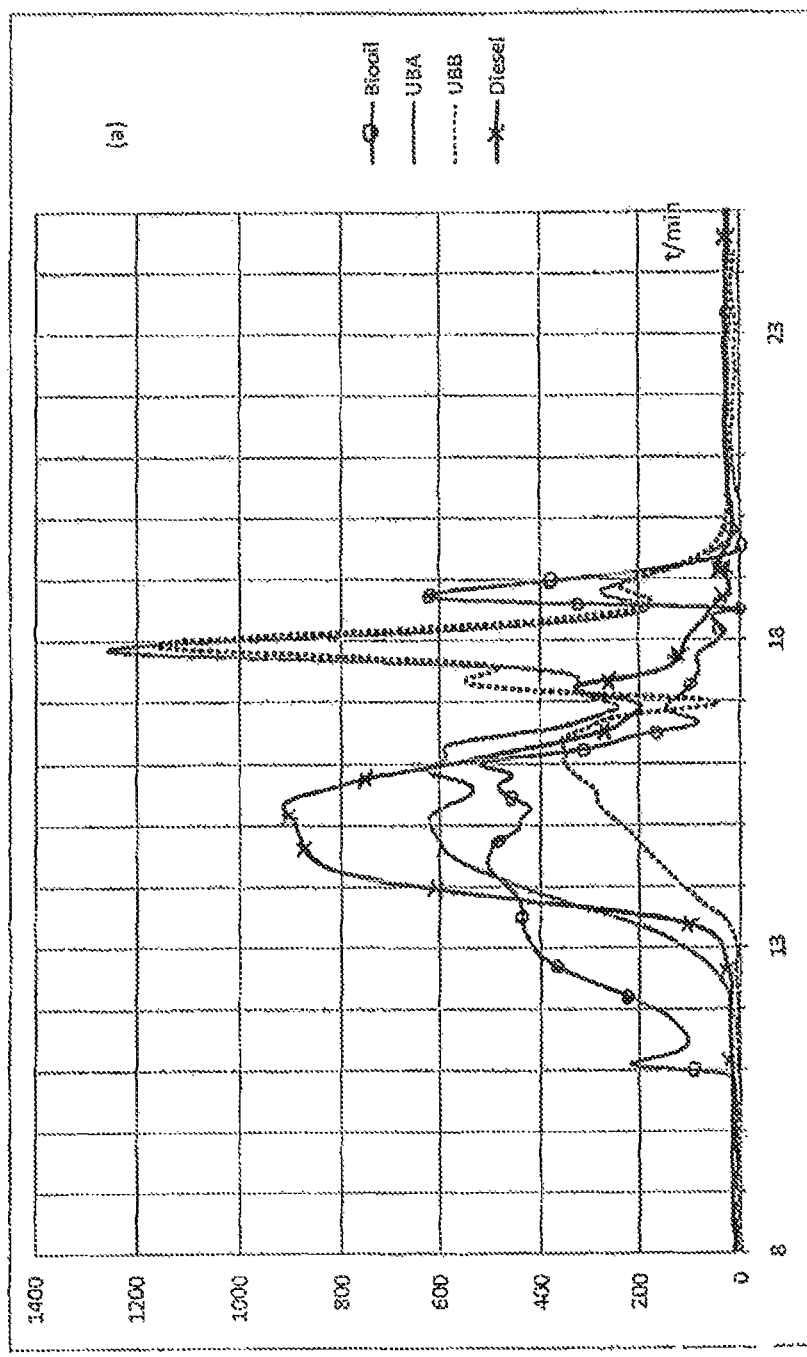
FIG. 4 illustrates the molecular weight distributions of the upgraded biooil products UBA and UBB.

Molecular weight (MW) distributions for samples of UBA and UBB, after being recycled at more than 90% roughly corresponding to a steady sate, were measured by gel permeation chromatography (GPC) on a Phenogel 5 u 50 A (Phenomenex) column eluted by tetrahydrofuran and calibrated with polystyrene standards. The results are illustrated in FIG. 4 where the unnormalized intensity data are plotted against elution time. Panel (a) compares raw biooil with UBA and UBB. The time is logarithmic in molecular weight so indicators corresponding to MWs~2000 and ~100 have been added to the figure. It is noticeable that polymerization reactions have been suppressed since the peak of high molecular weight components near MW 2000 in the raw biooil is essentially absent in UBA and UBB. At the same time the low molecular weight peak, contributed largely by water in biooil is also suppressed and overall, there is substantial narrowing of the MW distribution of biooil. The bulk of UBA corresponds to MW<1000 while the bulk of UBB corresponds to MW<500. UBB is compared with a No. 2 gasoline and diesel in panels (b) and (c) respectively. We conclude that the upgraded biooil products (both UBA and UBB) are bimodal mixtures of gasoline-like and diesel-like components.

A proton NMR spectrum of the product (UBB) is displayed in FIG. 5 and a $^{13}$C NMR spectrum in FIG. 6.

Figure 9:
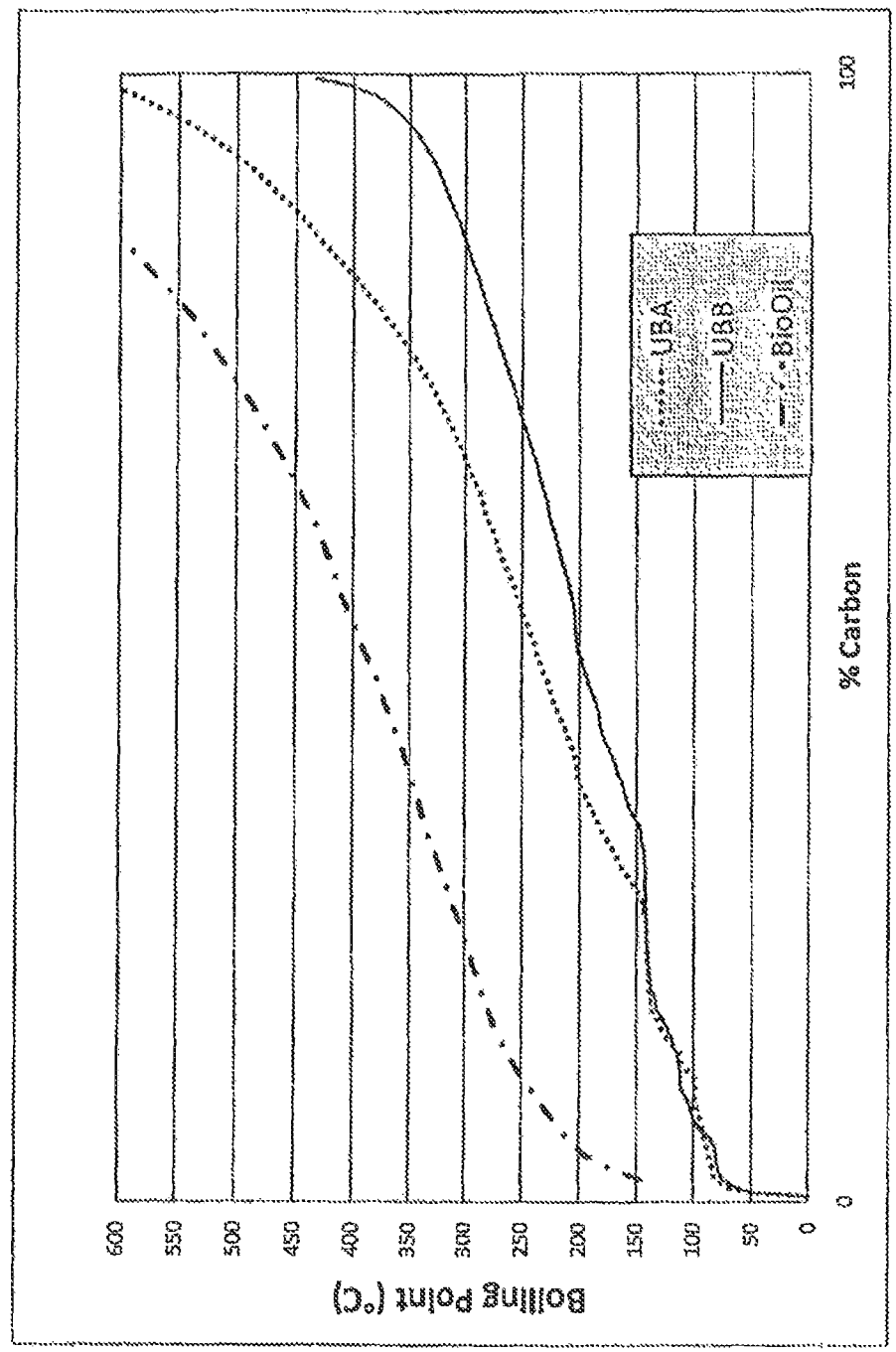
FIG. 9 shows Simulated Distillations of raw biooil, UBA and UBB.
Figure 10:
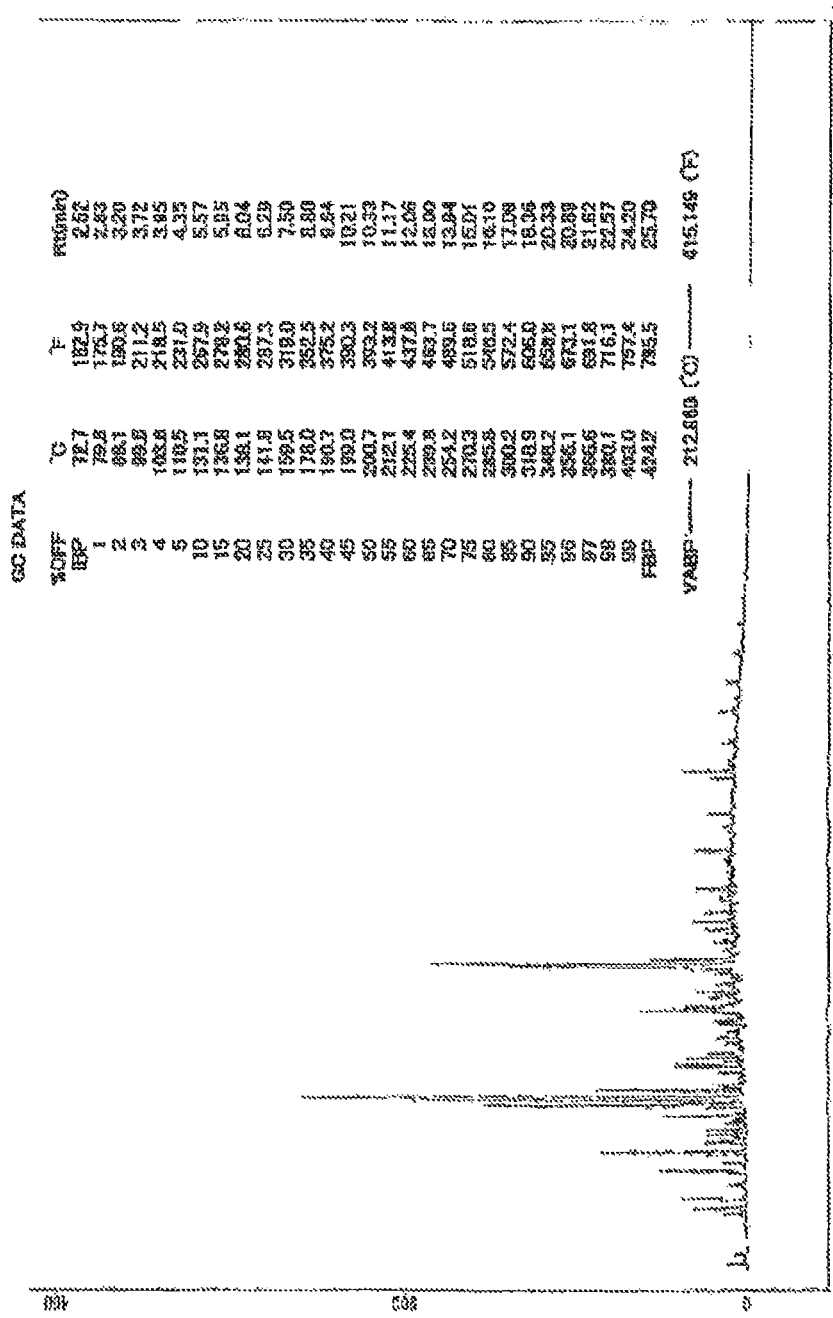
FIG. 10 shows the corresponding Gas Chromatogram of UBB.

Raw biooil along with UBA and UBB samples were also subjected to simulated distillation using capillary gas chromatography. The results are compared in FIG. 9. It is notable that UBB is pure distillate; i.e. it boils completely at less than 450° C. The corresponding gas chromatogram for UBB is shown in FIG. 10.

Example 12: Comparison of Various Transition Metal Catalysts in Batch Hydroreforming A variety of other transition metal catalysts on various supports were studied. The following examples describe a range of transition metals, singly and in combination, on activated carbon supports since activated carbon was found to be the most efficacious of the supports tested. The catalysts were prepared according to Example 1 with the appropriate soluble metal salts.

Batch experiments were carried out in the manner of Example 3. In all cases 4.5 g of the Metal/AC catalyst was reduced in situ after which about 66 g of a biooil, UBA and UBB mixture, in the proportions 2:1:1 respectively, was introduced into the autoclave reactor and the reaction allowed to proceed for 4 hrs at 330° C. under sufficient hydrogen (including nitrogen as tracer) to bring the total pressure to 1900 psia (13.1 MPa) at the reaction temperature. In most cases on cooling, the reaction mixture separated into two liquid phases, UBA and an aqueous phase. The results are summarized in the table below (table 8). The total mass of feed including biooil, UBA and UBB is given in column 3 while column 4 gives the mass ratio of oil (UBA) phase to aqueous phase of the products. In all cases the acetic acid content of the aqueous phase ranged between 7 to 12%. The next 3 columns give the density, water content and TAN of the oil phase. The next 5 columns contain the yields of various gases expressed as a mass % of the biooil used, while the last column gives the mass % of organics in the aqueous phase. Hydrogen is indicated as negative since it is consumed.

The precision of this test is exemplified by the results for a repetition of the test with Ni—Cr/AC (rows 1 &2). The runs marked with an asterisk (copper and molybdenum, runs 4 & 12) led to the formation of two oil phases. LUBA and HUBA. Overall the results confirm that a wide range of transition metals, singly or in combination, can catalyze the hydroreforming reaction under the conditions of this invention.

The manganese containing catalyst led to a low concentration of organics in the aqueous phase. Indeed the aqueous phase from the chromium and manganese catalysts (rows 1 & 11) were particularly noticeable for the near colourlessness of their aqueous phase products.

Zirconia and manganese appears to promote formation of $CO_2$, which is desirable as discussed in an earlier section, so it is not surprising that manganese led to the smallest consumption of hydrogen.

We conclude that hydroreforming may be carried out with a wide range of supported transition metal catalysts although nickel and chromium or manganese containing catalyst appears most effective.

TABLE 8

Comparison of various transition metal catalysts

| | | | Oil Phase (UBA) Properties | | | | Gas produced/Wt % of biooil | | | | | $[Org]_{Aq}$/ |
|---|---|---|---|---|---|---|---|---|---|---|---|---|
| | Catalyst | Feed/g | $M_{UBA}/M_{Aq}$ | $\rho$/g cm$^{-3}$ | $[H_2O]$/Wt % | TAN/ mg-KOH/g | $H_2$ | CO | $CH_4$ | $CO_2$ | $C_2+$ | Wt % |
| 1 | 10Ni—5Cr | 66 | 2.36 | 0.89 | 0.72 | 23 | −1.64 | 1.39 | 1.93 | 6.42 | 0.73 | 19.1 |
| 2 | 10Ni—5Cr | 64 | 2.36 | 0.90 | 0.64 | 22 | −1.70 | 1.25 | 1.84 | 6.13 | 0.49 | 19.3 |
| 3 | 10Ni—5Fe | 66 | 2.37 | 0.90 | 0.60 | 81.7 | −1.85 | 0.48 | 1.59 | 7.01 | 0.52 | 18.3 |
| 4 | 10Ni—5Cu* | 66 | 4.29 | 0.89 | 0.42 | 22* | −1.21 | 0.78 | 1.27 | 7.98 | 0.56 | 19.6 |
| | | | 1.43 | n.a. | n.a. | 81* | | | | | | |
| 5 | 10Ni | 64 | 2.33 | 0.91 | 1.05 | 30 | −1.56 | 0.62 | 0.75 | 6.89 | 0.30 | 18.6 |
| 6 | 10Ni—5Zr | 66 | 2.00 | 0.92 | 2.45 | 27 | −1.79 | 1.13 | 1.11 | 10.37 | 0.47 | 19.6 |
| 7 | 10Ni—5Ce | 62 | 3.09 | 0.90 | 0.50 | 22 | −1.28 | 0.50 | 0.90 | 7.39 | 0.28 | 14.8 |
| 8 | 10Ni—5CeZr | 68 | 1.98 | 0.93 | 1.69 | 80.1 | −1.77 | 1.27 | 1.37 | 10.87 | 0.40 | 19.7 |
| 9 | 10Ni—1Re | 67 | 2.19 | 0.90 | 0.80 | 21 | −1.50 | 0.94 | 1.10 | 7.13 | 0.51 | 19.7 |
| 10 | 10Ni—1Ru | 66 | 2.53 | 0.90 | 1.10 | 33 | −1.82 | 1.14 | 2.21 | 6.61 | 0.80 | 19.7 |
| 11 | 10Ni—5Mn | 68 | 2.47 | 0.90 | 0.50 | 23 | −1.22 | 0.46 | 0.88 | 9.56 | 0.31 | 16.6 |
| 12 | 10Ni—5Mo* | 68 | 2.12** | 0.90 | 0.75 | 26 | −1.32 | 0.43 | 1.80 | 6.78 | 0.46 | n.a. |
| | | | | | n.a. | n.a. | | | | | | |

*formation of two oil phases. LUBA and HUBA

Example 13: Comparison of Various Biooils in Batch Hydroreforming with Surfactant The composition of biooils varies within limited ranges by the nature of the biomass feedstock from which it was produced. Common pyrolysis feedstocks include hardwoods and softwoods, forestry clippings, crop wastes, e.g. wheat or corn straws, sugar cane bagasse, oil palm empty fruit bunches, etc. and sewage sludge.

Furthermore, on aging, biooils tend to be susceptible to condensation reactions that lead to increased water content and polymerization that can ultimately lead to spontaneous phase separation. Indeed, even some fresh biooils will phase separate if the biomass feedstock from which is produced naturally contains hydrophobic material like fats and waxes, or if it has a high proportion of water.

Most of the tests described herein were carried out with fresh hardwood biooils. It is therefore important to inquire into the applicability of the present invention to a wider variety of biooils from a wider variety of feedstocks. The following tests were carried out with various aged biooils that has been in storage for several years, and derived by pyrolysis of various biomass feedstocks. As a consequence they all had very high water content and multiple phases in some instances.

Hydroreforming batch experiments were carried out in a similar manner to Example 5 where the biooils were treated in xylene with Atlox 4919 as emulsifier (table 9). In each case about 30 g each of biooil and xylene containing 5% Atlox were treated with hydrogen using 4.5 g of 10Ni-5Cr/AC catalyst. (In case of the softwood derived biooils phase separation had occurred so they were homogenized by heating and stirring before sampling.) The reactions were carried out for four hours in flowing hydrogen at 330° C. and 1800 psia (12.4 MPa).

TABLE 9

Comparison of various biooils

| Biooil source | Water content Biooil/wt % | Density UBA/ g cm3 | TAN UBA/mg KOH g-1 | Water content UBA/wt % | Organics content Aq. Phase/wt % |
|---|---|---|---|---|---|
| Oil palm waste | 42 | 0.865 | 14 | 0.29 | 10.3 |
| Sugarcane Bagasse | 33 | 0.880 | 27 | 0.40 | 10.1 |
| Softwood bark | 40 | 0.875 | 21.3 | 0.16 | 9.9 |
| Softwood Clippings | 40 | 0.880 | 23 | 0.31 | 8.7 |

We conclude that the quality or biomass origin of the biooil is not a disabling factor for the inventive process.

The invention claimed is:

1. A method for treating a feed containing biooil comprising:
   (a) dispersing the feed containing biooil in a hydrocarbon liquid in the presence of a dispersing agent to obtain a dispersed mixture, wherein the hydrocarbon liquid is a biomass fuel derived hydrocarbon liquid and/or a recycled hydrocarbon liquid obtained from hydrotreating and/or hydrocracking and/or mild hydrocracking in step (d), and wherein the dispersing agent is (i) an oxygen-containing solvent, pure or blended, that is an alkanol, ketone, ester or phenolic compound, or (ii) a recycled partially upgraded biooil optionally with the hydrocarbon liquid contained in an organic phase obtained from hydroreforming in step (c), wherein the dispersing is conducted at a ratio of biooil/dispersing agent/hydrocarbon liquid of 2/4/2 to 2/1/0.5;
   (b) subjecting the dispersed mixture obtained from step (a) to hydroreforming with hydrogen in the presence of at least one transition metal catalyst, wherein the hydroreforming is carried out at an absolute pressure from about 3.8 MPa to 27.6 MPa;
   (c) separating an effluent from the hydroreforming in step (b) into an aqueous phase and at least one organic phase containing a partially upgraded biooil and the hydrocarbon liquid; and
   (d) hydrotreating and/or hydrocracking and/or mild hydrocracking the partially upgraded biooil optionally with the hydrocarbon liquid contained in the organic phase to produce a hydrocarbon liquid product.

2. The method according to claim 1, wherein the hydroreforming is carried out at a temperature from about 250° C. to about 450° C.

3. The method according to claim 1, wherein the organic phase contains less than about 15 mass % oxygen and less than about 2 mass % water.

4. The method according to claim 1, wherein the biooil contained in the feed is produced by fast or flash pyrolysis from biomass feedstock.

5. The method according to claim 1, wherein the at least one transition metal catalyst comprises a group 10 metal, singly or in combination with at least one metal of group 3 to group 12 of the periodic table, said catalyst being supported on a support.

6. The method according to claim 5, wherein the at least one transition metal catalyst comprise Ni, singly or in combination with at least one metal that is Ce, Zr, Cr, Mo, W, Mn, Re, Fe, Ru or Cu, and the support is porous carbon.

7. The method according to claim 5, wherein the catalyst is NiCr or NiMn on porous carbon.

8. The method according to claim 1, wherein step (d) comprises subjecting the partially upgraded biooil with or without the hydrocarbon liquid contained in the organic phase obtained from step (c) to the hydrotreating in the presence of hydrogen and a hydrotreating catalyst at a temperature between 250° C. and 450° C., at a pressure between 2 MPa and 25 MPa and at an hourly space velocity between 0.1 h$^{-1}$ and 20 h$^{-1}$.

9. The method according to claim 8, wherein the partially upgraded biooil with or without the hydrocarbon liquid contained in the organic phase is co-processed with a fossil derived feedstock.

10. The method according to claim 8, wherein the dispersing agent is the recycled partially upgraded biooil with or without the hydrocarbon liquid contained in the organic phase obtained from hydroreforminq in step (c), and wherein the hydrocarbon liquid is the recycled hydrocarbon liquid obtained from the hydrotreating and/or hydrocracking and/or mild hydrocracking in step (d).

11. The method according to claim 8, wherein an effluent obtained from the hydrotreating and/or hydrocracking and/or mild hydrocracking is further subjected to a high pressure hydrocracking in the presence of hydrogen and a hydrocracking catalyst at a temperature between 250° C. and 480° C., at a pressure between 2 and 25 MPa, and an hourly space velocity between 0.1 h$^{-1}$ and 20 h$^{-1}$.

12. The method according to claim 1, wherein step (d) comprises subjecting the partially upgraded biooil with or without the hydrocarbon liquid contained in the organic phase obtained from step (c) to the hydrocracking in the presence of hydrogen and a hydrocracking catalyst at a temperature over 200° C., at a pressure between 2 and 25 MPa and at an hourly space velocity between 0.1 h$^{-1}$ and 20 h$^{-1}$.

13. The method according to claim 1, wherein step (d) comprises subjecting the partially upgraded biooil with or without the hydrocarbon liquid contained in the organic phase to the mild hydrocracking in the presence of hydrogen and a hydrocracking catalyst at a temperature between 250° C. and 480° C., at a pressure between 2 MPa and 12 MPa and an hourly space velocity between 0.1 h$^{-1}$ and 20 h$^{-1}$.

* * * * *